United States Patent
Ohno et al.

(10) Patent No.: US 7,385,035 B2
(45) Date of Patent: Jun. 10, 2008

(54) CYTOTOXIC PROTEIN AND UTILIZATION THEREOF

(75) Inventors: Hiroyuki Ohno, Chiba (JP); Hiromitsu Saisho, Tokyo (JP); Hideki Tanzawa, Chiba (JP)

(73) Assignee: Fourier Inc., Chiba (JP)

( * ) Notice: Subject to any disclaimer, the term of this patent is extended or adjusted under 35 U.S.C. 154(b) by 467 days.

(21) Appl. No.: 10/496,384

(22) PCT Filed: Dec. 5, 2002

(86) PCT No.: PCT/JP02/12752

§ 371 (c)(1),
(2), (4) Date: May 24, 2004

(87) PCT Pub. No.: WO03/048199

PCT Pub. Date: Jun. 12, 2003

(65) Prior Publication Data

US 2006/0210575 A1    Sep. 21, 2006

(30) Foreign Application Priority Data

Dec. 5, 2001    (JP)    ............... 2001-371210

(51) Int. Cl.
*C07K 5/10* (2006.01)
(52) U.S. Cl. .................. 530/350; 435/810
(58) Field of Classification Search .......... None
See application file for complete search history.

(56) References Cited

U.S. PATENT DOCUMENTS

| | | | |
|---|---|---|---|
| 4,800,155 A | 1/1989 | Taniguchi et al. | |
| 5,024,946 A | 6/1991 | Abe et al. | |
| 5,093,261 A | 3/1992 | Hagiwara et al. | |
| 5,366,865 A | 11/1994 | Gralnick | |
| 5,776,427 A | 7/1998 | Thorpe et al. | |
| 5,863,538 A | 1/1999 | Thorpe et al. | |
| 5,877,289 A | 3/1999 | Thorpe et al. | |
| 6,004,555 A | 12/1999 | Thorpe et al. | |
| 6,093,399 A | 7/2000 | Thorpe et al. | |
| 6,417,337 B1 | 7/2002 | Anderson et al. | |
| 6,753,420 B2 | 6/2004 | Anderson et al. | |
| 6,787,153 B1 | 9/2004 | Hosokawa et al. | |
| 6,887,474 B1 | 5/2005 | Stewart et al. | |
| 2002/0061569 A1* | 5/2002 | Haselbeck et al. | .......... 435/183 |

FOREIGN PATENT DOCUMENTS

WO    WO 97/37044    * 10/1997

OTHER PUBLICATIONS

U.S. Appl. No. 11/049,118, filed Oct. 2005, Awdalla.
U.S. Appl. No. 11/149,515, filed Dec. 2005, Nichols et al.
U.S. Appl. No. 11/205,045, filed Dec. 2005, Stewart et al.
Brown, J. M. "Exploiting the hypoxic cancer cell: mechanisms and therapeutic strategies." Molecular Medicine Today Apr. 2000 (vol. 6).
Paganelli G, Riva P, Deleide G, et al,In vivo labelling of biotinylated monoclonal antibodies by radioactive avidin: a strategy to increase tumor radiolocalization, Int J Cancer Suppl. 1988; 2: 121-125.
P. Webber et al., "Structural origins of high-affinity biotin binding to streptavidin" Science, vol. 243, pp. 85-88, Jan. 6, 1989.
M. Wilchek et al, The avidin-biotin complex in bioanalytical applications Analytical Biochemistry, vol. 171 pp. 1-32, 1988.
Bayer et al., "The Avidin-Biotin Complex as a Tool in Molecular Biology", Trends in Biochemical Science, 3, N257, Nov. 1978.
Otto C. Boerman et al., "Pretargeted Radioimmunotherapy of Cancer: Progress Step by Step", Journal of Nuclear Medicine vol. 44 No. 3 400-411.
Kohler and Milstein, Nature, 256: 495-97, 1975; Eur. J. Immunol., 6: 511-19, 1976.
Hechler, B., Leon, C., Vial, C., Vigne, P., Frelin, C., Cazenave, J. P., and Gachet, C. (1998) Blood 92, 152-159.
Duijvestijn et al., "Lymphoid Tissue- and Inflammation-Specific Endothelial Cell Differentiation defined by Monoclonal Antibodies," The Journal of Immunology, 138(3):713-719, 1987.
Hagemeier et al., "A Monoclonal Antibody Reacting with Endothelial Cells of Budding Vessels in Tumors and Inflammatory Tissues, and Non-Reactive with Normal Adult Tissues," International Journal of Cancer, 38:481-488, 1986.
Bruland et al., "New Monoclonal Antibodies Specific for Human Sarcomas," International Journal of Cancer, 38:27-31, 1986.
Murray et al., "Vascular Markers for Murine Tumours," Radioherapy and Oncology, 16:221-234, 1989.
Schlingemann et al., "Monoclonal Antibody PAL-E Specific for Endothelium," Laboratory Investigation, 52(1):71-76, 1985.
Shrestha et. al., Eur. J. Cancer B. Oral. Oncol., 30B(6):393-9, 1994.
Tuominen and Kallioinen, J. Cutan. Pathol. 21(5):424-9, 1994.
American Cancer Society: Cancer Facts and Figures 2005.

* cited by examiner

*Primary Examiner*—Misook Yu
*Assistant Examiner*—Mark Halvorson
(74) *Attorney, Agent, or Firm*—Browdy and Neimark, PLLC

(57) ABSTRACT

This invention relates to a new cytotoxic protein (M toxin, mucous layer devastating toxin) produced by *Helicobacter pylori* and the use.

This invention provides a cytotoxic protein (M toxin) produced by *Helicobacter pylori*, a partial peptide, and an antitumor agent containing the cytotoxic protein. The protein is obtained by culturing a transformant which is transformed with a recombination vector containing DNA coding the cytotoxin protein. This invention provides further the use of the protein.

6 Claims, 8 Drawing Sheets

No.116  No.4  No.101

SEQUENCE LISTING

<160> NUMBER OF SEQ ID NOS: 4

<210> SEQ ID NO 1
<211> LENGTH: 357
<212> TYPE: PRT
<213> ORGANISM: Helicobacter pylori

<400> SEQUENCE: 1

```
Met Lys Gly Leu Glu Arg Glu Ser His Phe Thr Leu Asp Glu Asn Ala
1               5                   10                  15

Met Phe Phe Glu Cys Ala Tyr Ser Cys Asp Asn Ala Leu Phe Leu Gln
            20                  25                  30

Leu Glu Asp Arg Ser Phe Phe Ile Thr Asp Ser Arg Tyr Thr Gln Glu
        35                  40                  45

Ala Lys Glu Ser Ile Gln Pro Lys Asn Gly Val Leu Ala Glu Val Ile
    50                  55                  60

Glu Ser Ser Asp Leu Val Gln Ser Thr Ile Asp Leu Ile Ala Lys His
65                  70                  75                  80

Ser Val Lys Lys Leu Phe Phe Asp Pro Asn Gln Val Asn Leu Gln Thr
                85                  90                  95

Tyr Lys Arg Leu Asp Ser Ala Ile Gly Asn Lys Val Ile Leu Glu Gly
            100                 105                 110

Val Pro Ser Tyr His Arg Gln Lys Arg Ile Ile Lys Asn Asn His Glu
        115                 120                 125

Ile Gln Leu Leu Lys Lys Ser Gln Ala Leu Asn Val Glu Ala Phe Glu
    130                 135                 140

Asn Phe Ala Glu Tyr Val Lys Lys Ile Phe Asp Glu Lys Glu Ser Leu
145                 150                 155                 160

Ser Glu Arg Tyr Leu Gln His Lys Val Lys Asp Phe Leu Thr Lys Glu
                165                 170                 175

Gly Val Tyr Asp Leu Ser Phe Glu Pro Ile Leu Ala Leu Asn Ala Asn
            180                 185                 190

Ala Ser Lys Pro His Ala Leu Pro Ser Ala Lys Asp Phe Leu Lys Ala
        195                 200                 205

Glu His Ser Ile Leu Leu Asp Met Gly Ile Lys Tyr Glu Arg Tyr Cys
    210                 215                 220

Ser Asp Arg Thr Arg Thr Ala Phe Phe Asp Pro Lys Asp Phe Val Phe
225                 230                 235                 240

Lys Arg Glu Gln Ser Phe Lys Asp Lys Glu Ser Gln Lys Ile Tyr Asp
                245                 250                 255

Ile Val Lys Glu Ala Gln Glu Lys Ala Ile Ser Gly Ile Arg Ala Gly
            260                 265                 270

Met Thr Gly Lys Glu Ala Asp Ser Leu Ala Arg Gly Val Ile Ser Asp
        275                 280                 285

Tyr Gly Tyr Gly Gln Tyr Phe Thr His Ser Thr Gly His Gly Ile Gly
    290                 295                 300

Leu Asp Ile His Glu Leu Pro Tyr Ile Ser Ser Arg Ser Glu Thr Ile
305                 310                 315                 320

Leu Glu Glu Gly Met Val Phe Ser Val Glu Pro Gly Ile Tyr Ile Pro
                325                 330                 335
```

```
Gly Phe Phe Gly Val Arg Ile Glu Asp Leu Val Val Ile Lys Asn Ser
            340                 345                 350

Arg Ala Glu Leu Leu
        355

<210> SEQ ID NO 2
<211> LENGTH: 1071
<212> TYPE: DNA
<213> ORGANISM: Helicobacter pylori

<400> SEQUENCE: 2
atgaaaggat tagaaagaga atcgcatttc acgcttgatg aaaacgcgat gttttttgag      60
tgtgcttata gttgcgataa tgctttgttt ttgcaattag aggatcgctc gttttttatc     120
actgattctc gctacactca agaagctaaa gaaagcattc agcctaaaaa tggcgttta     180 gcggaagtga tagaatccag cgatttagtc caaagcacga ttgatttgat cgcaaaacac     240
tcggttaaaa agctcttttt tgatcccaat caagtgaatt tgcaaaccta caagcgtttg     300
gattcggcga ttgggaataa ggttatttta gagggcgtgc ctagttacca ccgccaaaaa     360
cgcatcatta aaacaatca tgagatccaa ctcctcaaaa aatctcaagc gttgaatgtt     420
gaagcttttg aaaattttgc cgagtatgtg aaaaagattt ttgatgaaaa agagtccttg     480
agcgagcggt atttgcagca taaggttaag gacttttga ctaaagaggg ggtttatgat      540
ctgagctttg agcctatttt agccttgaat gcgaacgcga gcaaaccccca tgctttgcct     600 agtgcgaagg atttttaaa agcggagcat agcattcttt tggatatggg gatcaaatac      660
gaacgctatt gctcggatag gactcgcacg gctttttttg accctaaaga ttttgtcttc     720
aaaagagagc agagtttcaa ggataaagag agtcaaaaga tttatgacat tgtgaaagaa     780
gcgcaagaaa aggctatttc aggtattaga gcgggcatga ccgtaaaga agcggacagc      840 ttggctaggg gagtgattag cgattatggt tatgggcaat atttcactca cagcactgga     900
catggcattg gcttagacat tcatgagctt ccttatattt catcgcgcag tgaaaccatt     960
ttagaagagg gcatggtgtt ttctgtagag cctgggattt atatccctgg attttttggg    1020
gtgcgcattg aagatttagt ggtgatcaaa aattctaggg ctgagctttt g              1071

<210> SEQ ID NO 3
<211> LENGTH: 32
<212> TYPE: DNA
<213> ORGANISM: Helicobacter pylori

<400> SEQUENCE: 3
gacgacgaca agatgaaagg attagaaaga ga                                    32

<210> SEQ ID NO 4
<211> LENGTH: 37
<212> TYPE: DNA
<213> ORGANISM: Helicobacter pylori

<400> SEQUENCE: 4
gaggagaagc ccggttacaa aagctcagcc ctagaat                               37
```

CYTOTOXIC PROTEIN AND UTILIZATION THEREOF

FIELD OF THE INVENTION

This invention relates to a new cytotoxic protein (M toxin, mucous layer devastating toxin) produced by *Helicobacter pylori* and the use.

BACKGROUND ART

It has been considered that the human gets many gastritis, gastric ulcer and gastric cancer by *Helicobacter pylori*. A distinct direct cytotoxic factor causing destruction of gastric epithelial cells and irreversible cell death at the beginning of these diseases has not been specified. A factor changing pH environment and immunity reaction in the stomach, a factor adhering to gastric epithelial cells by *Helicobacter pylori*, or move properties of bacteria themselves has been indicated as a factor developing such diseases. However, it has been unclear hitherto that gastric mucosal destruction triggering gastritis, gastric ulcer and gastric cancer is injured in any process, or what is a direct responsible factor to the gastric mucosal destruction. The only is that vacuolating toxin having cytotoxicity is isolated, but it has week cytotoxic activity and reversible cytotoxic activity. As a fatal cytotoxic factor of a pathogenic factor, it has not been found in vivo and in vitro.

Many researchers estimate that *Helicobacter pylori*, as described in the above, in the environment stomach in vivo, secretes a direct cytotoxic factor for gastric mucosal cells. Considering the importance of diseases, all sequences of the gene is confirmed in 1996. However, in spite of the use of serum, it is impossible to isolate and identify the presumable toxin due to separation conditions, with difficult culture conditions and purification conditions and unfixed valuation systems of the toxin.

Problems to be Solved by the Invention

One problem is that responsible protein causing gastritis, gastric ulcer and gastric cancer by *Helicobacter pylori* infection is found, a mass production method of the toxic protein is established, new M toxin is identified, and diagnosis and screening method is established. Using these methods, it is desired that responsible toxin of a cytotoxic factor for gastric mucosal cells is controlled, and preventive and treating agents of gastritis, gastric ulcer, gastric cancer and the like are developed and a method for using the toxin is found.

DISCLOSURE OF THE INVENTION

Inventors of this invention have studied earnestly to resolve the above-mentioned problem, and identified a new toxin that causes irreversible cell death when *Helicobacter pyloriis* cultured under serum-free conditions that is similar to environment in the stomach different from usual. It has been found that this toxin has a toxic power 1000 to 100000 times per unit of above-mentioned vacuolating toxin, and it causes irreversible cell death for various warm-blooded animal cells comprising not only gastric epithelial cells but also immunocytes. The inventors of this invention have repeatedly researched on these views to attain to the present invention.

Namely, this invention provides the following. (1) A cytotoxic protein comprising a protein having at least 70% or more identity for the amino acid sequence represented by SEQ ID No. 1. (2) A partial peptide of the cytotoxic protein described in claim 1, characterized in that the protein has the same cytotoxic activity as that of the amino acid sequence represented by SEQ ID No. 1. (3) The cytotoxic protein of claim 1 or claim 2 wherein the protein is produced with *Helicobacter pylori*. (4) The cytotoxin protein of claim 1 or claim 2 wherein the protein is obtained by culturing a transformant which is transformed with a recombination vector containing DNA of SEQ ID No. 2 coding the cytotoxin protein of claim 1 or 2. (5) The cytotoxin protein of claim 4 wherein the transformant is deposited by deposition No. FERM BP-8218 at National Institute of Advanced Industrial Scienc and Technology (IPOD). (6) An antitumor agent which contains the cytotoxic protein of claim 1 or 2. (7) A monoclonal antibody specific against the cytotoxic protein which is obtained by immunization of the cytotoxic protein of claim 1 or 2 against a mammal. (8) The monoclonal antibody of claim 7 which is produced with a hybridoma done of deposition No. FERM BP-8222. (9) The monoclonal antibody of claim 7 which is produced with a hybridoma clone of deposition No. FERM BP-8223. (10) The monoclonal antibody of claim 7 which is produced with a hybridoma done of deposition No. FERM BP-8224. (11) A polyclonal antibody specific against the cytotoxic protein which is obtained by immunization of the cytotoxic protein of claim 1 or 2 against a mammal. (12) A method for detecting and diagnosing the cytotoxic protein of claim 1 or 2 wherein the monoclonal antibody or polyclonal antibody described in any one of claims 7-11 is used. (13) An agent for preventing and treating gastric cancer, gastritis and gastric ulcer triggered by the cytotoxic protein of claim 1 or 2, wherein the monoclonal antibody or polyclonal antibody described in any one of claims 7-11 are used. (14) A method for screening a compound promoting or inhibiting activity of the protein of claim 1 or 2, wherein cell multiplication inhibition activity, cytotoxic activity or cell death is judged by comparison between negative or positive control groups with a warm-blooded animal cell. (15) A kit for screening a compound or its salt promoting or inhibiting activity of the protein of claim 1 or 2, wherein the protein of claim 1 or 2 is comprised. (16) A compound or its salt promoting or inhibiting activity of the protein of claim 1 or 2, wherein the compound is obtained by the screening method of claim 14 or with the kit for screening of claim 15. (17) A medicine containing a compound or its salt, wherein the compound has activity inhibiting cytotoxic activity of warm-blooded animal cells with the protein of claim 1 or 2. (18) A medicine of claim 17, which is an agent for preventing or treating gastritis, gastric ulcer, gastric cancer and a disease showing that it is caused with M toxin by the screening method of cliam 14 or with the screening kit of claim 15.

BEST MODE FOR CARRYING OUT THE INVENTION

Figure 1:
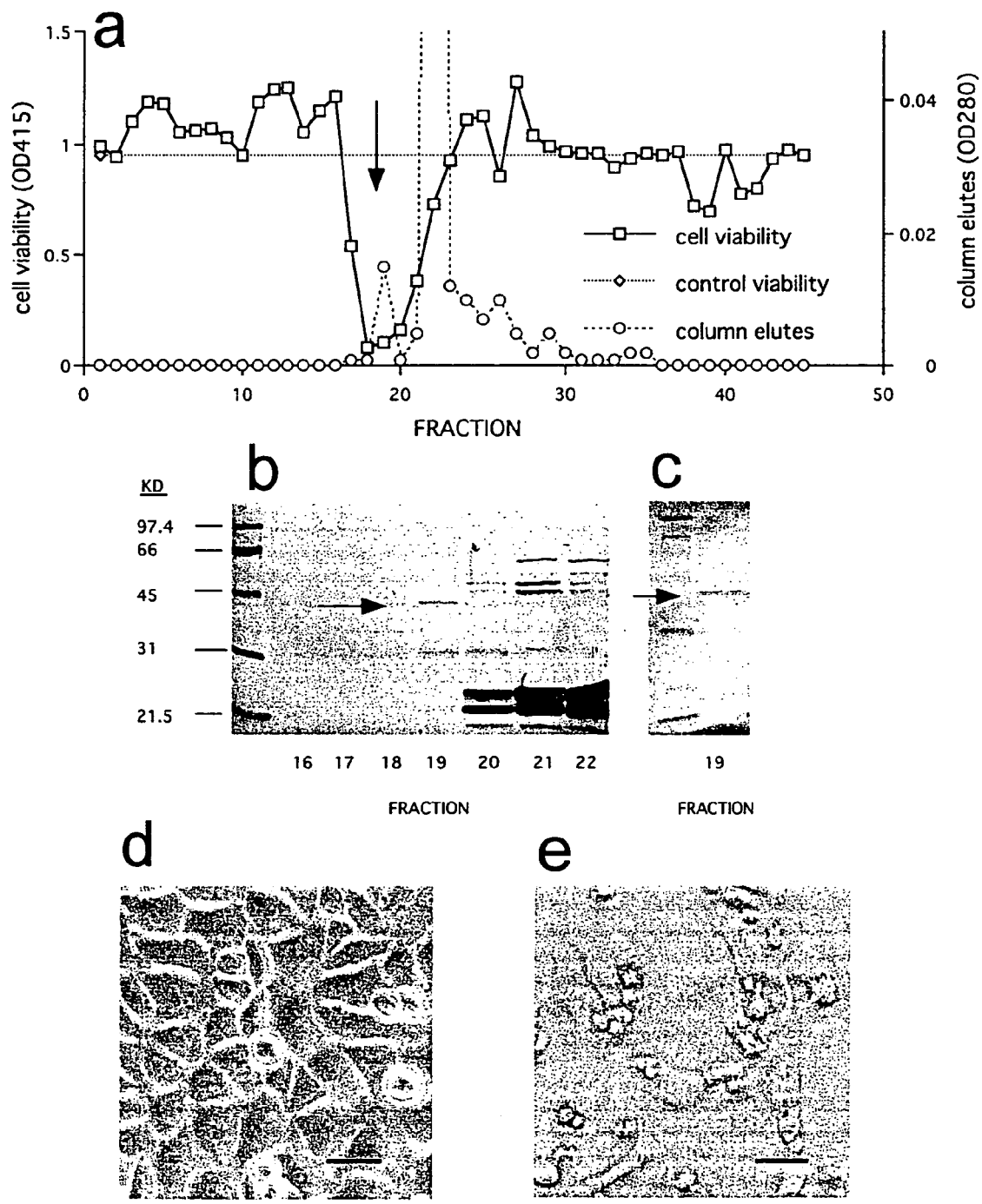
FIG. 1 shows an anion exchange chromatography of the sample obtained in Example 1. a shows activity of M toxin for each fraction and absorbances of the elute protein. b shows SDS-PAGE by silver stain of fraction 16 to fraction 22 in the chromatography of a. c shows bands of protein toxin transferred to a PVDF membrane by electroblotting. d and e show morphologic changes of HeLa cell 24 hours after exposure to the control extract and the cytotoxin including extract at a concentration of 1 nM, respectively. Scale bar, 50 µm.

The protein having the same amino acid sequence or substantially identical amino acid sequence with the amino acid sequence represented by SEQ ID No.1 of this invention may be a protein originating from bacteria strains of *Helicobacter pylori*, for example, NCTC 11637, NCTC 11916, DT 61A, NCTC 11639, R85-13 6P, R85-13-12F, R85-13-11P, T81213-NTB, J99, 4, U2-185D08, MC903, MC123, Tx30a, 26695, UA 1182 and the like, or my be a synthesized protein.

As substantially the same amino acid sequence as the amino acid sequence represented by SEQ ID No. 1, amino acid sequences having homology of about 70% or more, preferably about 80% or more, more preferably about 90% or more, further more preferably about 95% or more can be exemplified. As a protein having substantially the same amino acid sequence as the amino acid sequence represented by SEQ ID No.1, a protein having substantially the same amino acid sequence and substantially the same activity as that of the protein having the amino acid sequence represented by SEQ ID No. 1 can be exemplified. As substantially the same activity, a cell multiplication inhibition activity, a cytotoxic activity or an activity causing cell death can be exemplified. The term of substantially the same means that these activities have tha same quality, for example, in physiological chemistry or pharmacology. Accordingly, it is preferred that the activity of cytotoxin and the like has the same quality, for example, about 0.1-100 times, preferably about 0.5-10 times, more preferably about 0.5-2 times. The degree of these activities or quantity factors of molecular weights of proteins may be different. The activities of a cell multiplication inhibition activity, a cytotoxic activity or an activity causing cell death can be determined by well-known methods, for example, by the screening method undermentioned.

As the protein of this invention, the following proteins can be exemplified: an amino acid sequence deleting 1-150 (preferably 1-50) amino acids in the amino acid sequence represented by SEQ ID No.1; an amino acid sequence adding 1-100 (preferably 1-30) amino acids in the amino acid sequence represented by SEQ ID No. 1; an amino acid sequence inserting 1-50 (preferably 1-30) amino acids in the amino acid sequence represented by SEQ ID No. 1; an amino acid sequence that 1-50 (preferably 1-30) amino acids in the amino acid sequence represented by SEQ ID No. 1 are substituted by the other amino acids; or a protein containing a combination of these amino acid sequences, what is called mucin.

When an amino acid sequence is iserted, deleted or substituted as described in the above, the position of insertion, deletion or substitution is not specifically limited.

In the protein of this specification, according to a usual practice, the left side is an N end (an amino end) and the right side is a C end (a carboxyl end). In the proteins of this invention, which comprises the protein having the amino acid sequence represented by SEQ ID No.1, the C end is usually a carboxyl group (—COOH) or a carboxylate (—COO—), but it may be an amid (—CONH$_2$) or an ester group (—COOR), wherein R is a $C_{1-6}$ alkyl group of methyl, ethyl, n-propyl, isopropyl, n-butyl and the like, a $C_{3-8}$ cycloalkyl group of cyclopentyl, cyclohexyl and the like, a $C_{6-12}$ aryl group of phenyl, α-naphthyl and the like, benzyl, phenetyl and the like, a phenyl-$C_{1-2}$ alkyl group of benzyl, phenetyl and the like, or a $C_{7-14}$ aralkyl group of an α-naphthyl-$C_{1-2}$ alkyl group of α-naphthylmethyl and the like. When the protein of this invention has a carboxyl group (or carboxylate) at a position other than the C end, proteins having an amidic or esterified group are contained in the protein of this invention. As the ester, the ester of the above-mentioned C end may be used. In the proteins of this invention, further, there is a protein that the amino group of an amino acid residue (for example, a methionin residue) at the N end is protected by a protective group (for example, a $C_{1-6}$ acyl group of a $C_{1-6}$ alkanoyl group or the like of a formyl group, acetyl group or the like); a protein that the glutamic acid residue of the N end produced by incision in vivo is changed into pyrroglutamic acid group; a protein that the substituent group on the side chain of an amino acid in the molecular (for example, —OH, —SH, an amino group, an imidazole group, an indol group, a guanidino group or the like) is protected by a suitable protective group (for example, a $C_{1-6}$ acyl group or the like of $C_{1-6}$ alkanoyl group or the like of a formyl group); or a conjugated protein or the like of so-called glycoproteins that the sugar chain is bound.

As the partial peptide of the protein of this invention, it may be a partial peptide of the above-mentioend proteins of this invention, and preferably, it has similar activities (for example, a cell multiplication inhibition activity, a cytotoxic activity or the like) to the proteins of this invention. As an example, a peptide of an amino acid sequence having at least 20% or more, preferably 50% or more, more preferably 70% or more, further preferably 90% or more, and most preferably 95% or more in the amino acid sequence of this invention, and having a cell multiplication inhibition activity, a cytotoxic activity or an activity causing cell death can be utilized. The partial peptide of this invention may be the following peptides: 1-5 (prederably 1-3) amino acids are deleted in the amino acid sequence; 1-10 (preferably 1-5 (more preferably 1-3)) amino acids added to the amino acid sequence; 1-5 (preferably 1-3) amino acids are inserted into the amino acid sequence; or 1-5 (preferably 1-3) amino acids are substituted by the other amino acids.

Although the partial peptide of this invention has usually a carboxyl group (—COOH) or carboxylate (—COO—) at the C end, as shown in the above proteins of this invention, the C end may be amide (—CONH$_2$) or ester (COOR) wherein R is the same meaning as shown in the above. In the partial peptide of this invention, further, as shown in the above proteins of this invention, there is a peptide that the amino group of an amino acid residue (for example, a methionin residue) at the N end is protected by a protective group; a protein that the glutamic acid residue of the N end produced by incision in vivo is changed into pyrroglutamic acid group; a protein that the substituent group on the side chain of an amino acid in the molecular is protected by a suitable protective group; or a conjugated protein or the like of so-called glycoproteins that the sugar chain is bound. The partial peptide of this invention can be used as an antigen for constructing an antibody, so that a cell multiplication inhibition activity, a cytotoxic activity or the like is no necessarily required.

As the salt of the protein or partial peptide of this invention, salts of physiologically allowable acids (for example, inorganic acids or organic acids) or bases (for example, alkali metal salts) can be used, and preferably physiologically allowable acid addition salts, can be used. As such salts, for example, there are salts of inorganic acids (for example, hydrochloric acid, phosphoric acid, hydrobromic acid, sulfuric acid), organic acids (for example, acetic acid, formic acid, propionic acid, fumaric acid, maleic acid, succinic acid, tartaric acid, citric acid, malic acid, oxalic acid, benzoic acid, methane sulfonic acid, benzene sulfonic acid). The proteins and the salts of this invention can be produced by well-known preparation methods of proteins from any kinds of strains of above-mentioned *Helicobacter pylori*, or by culturing a transformant containing DNA that after-mentioned protein is coded. They further can be produced in accordance with after-mentioned method for syntheizing peptides. When the proteins are produced from any kinds of strains of *Helicobacter pylori*, proteins in bacterial cells are centrifuged off by ultrsonic crushing, then they are extracted by ammonium sulfate precipitation or the like, and the extracted liquid is purified and separated by combined chromatography such as ion exchange chromatography and hydrophobic chromatography.

In the synthesis of the protein, the partial peptide, salts thereof or amide thereof of this invention, commertially available resins for synthesizing proteins can be used. As such resins, the following resins can be exemplified: chloromethyl resin, hydroxymethyl resin, benzhydrylamine resin, aminomethyl resin, 4-benzyloxybenzylalcohol resin, 4-methylbenzhydryl-amine resin, PAM resin, 4-hydroxymethylmethylphenylacetoamidemethyl resin, polyacrylamide resin, 4-(2',4'-dimethoxyphenylhydroxymethyl)phenoxy resin, 4-(2',4'-dimethoxyphenyl-Fmoc aminoethyl) phenoxy resin. Using such resins, an amino acid that α-amino groups and functional groups of side chains are suitably protected is condensed on the resin to meet to the desired protein sequence by a well-known condensation method. At the end of reaction, the protein is cut off from the resin and several protecting groups are deleted. Then, the desired proteins or amides thereof are obtained by a method for forming internal disulfide bonds in a high dilution solution. Concerning the above-mentioned condensation of protected amino acids, several kinds of activated agents for protein synthesis can be used, and particularly, carbodiimides can be used. As such carbodiimides, DCC, N,N'-diisopropylcarbodiimide, N-ethyl-N'-(3-dimethylaminopropyl)carbodiimide and the like can be used. In activation by these carbodiimides, the protected amino acid can be directly added to the resin with an additional agent for controlling racemization (for example, HOBt or HOOBt), or it can be added to the resin after previous activation of the protected amino acid as a symmetric acid anhydride or, HOBt ester or HOOBt ester.

As the solvent used in the activation of the protected amino acid or the condensation with the resin, it can be selected from known solvents usable for the protein condensation reaction. As such solvent, acid amides such as N,N-dimethylformamide, N,N-dimethylacetoamide and N-methylpyrolidone, halogenated hydrocarbons such as methylene chloride and chloroform, alcohols such as trifuloroethanol, sulfoxydes such as dimethylsulfoxide, pyridine, eters such as dioxane and tetrahydrofuran, nitriles such as acetonitrile and propionitrile, esters such as methyl acetate and ethyl acetate, and mixtures thereof can be used. The reaction temperature is suitably selected from the known ranges that can be used in the reaction for forming protein bonds, and usually, it is suitably selected from −20° C.~50° C. Activeted amino acid derivatives are usually used by 1.5-4 times of the mole equivalent. As a test result of ninhydrin reaction, when the condensation is insufficient, the condensation reactions can be repeated without the deletion of the protected groups to conduct sufficient condensation. When sufficient condensation can not be conducted by the repeated reactions, unreacted amino acids are acetylated with acetic anhydride or acety imidazole, so that subsequent reactions have no influence.

As the protected groups of amino groups of starting materials, for example, Z, Boc, t-pentyloxycarhonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulfenyl, diphenylphosphinothioyl, Fmoc and the like can be used. The carboxyl groups can be protected, for example, by alkyl-esterification (for example, alkylesteration of straight, branched or cyclic chains of methyl, ethyl, propyl, butyl, t-butyl, cyclopentyl, cyclohexyl, cycloheptyl, cyclooctyl and 2-adamantyl), aralkylesteration (for example, benzylester, 4-nitrobenzylester, 4-methoxybenzylester, 4-chlorobenzylester, benzhydrylester), phenacylesteration, benzyloxycarbonylhydradidation, t-butoxycarbonylhydradidation, tritylhydradidation and the like. The hydroxyl group of serine can be prtected, for example, by esterification or etheration. As the suitable groups of this esterification, for example, lower (C$_{1-6}$) alkanoyl groups such as an acetyl group, an acyl group such as a benzoyl group, or groups derived from carbonate such as a benzyloxycarbonyl group and ethoxycarbonyl group can be used. As groups suitable to the etheration, a benzyl group, a tetrahydropyranyl group and a t-butyl group can be exemplified. As the protected groups of phenolic hydroxyl groups of tyrosine, for examle, Bzl, C$_{12}$-Bzl, 2-nitrobenzyl, Br-Z and t-butyl can be used. As the protected groups of imidazole of histidine, for example, Tos, 4-methoxy-2,3,6- trimethylbenzenesulfonyl, DNP, benzyloxymethyl, Bum, Boc, Trt and Fmoc can be used.

As the activated carboxyl groups of starting materials, for example, corresponding acid anhydrides, azides and activated esters (esters of alcohol (for example, pentachlorophenol, 2,4,5-trichlorophenol, 2,4-dinitrophenol, cyanomethylalcohol, paranitrophenol, HONB, N-hydroxysuccimide, N-hydroxyphthalimide and HOBt)) can be used. As the activated amino groups of starting materials, for example, corresponding phosphoric amides can be used. As a method for removing (elimination) of the protected groups, for example, catalytic reduction in hydrogen stream in the presence of a catalyst of Pd-black or Pd-charcoal; acid treatment with anhydrous hydrogen fluoride, methan sulfonic acid, trifluoromethan sulfonic acid, trfluoroacetic acid or their mixtures; base treatment with diisopropylethylamine, triethylamine, piperidine, piperadine or the like; or reduction with sodium in liquid ammonia can be used. The elimination reaction by using the above acid treatment is conducted usually at a temperature of −20° C.~−40° C. In the acid treatment, it is efficient to add a cation catching agent such as anisol, phenol, thioanisol, metacresol, paracresol, dimethylsulfide, 1,4-butandithiol or 1,2-ethandithiol. The 2,4-dinitrophenyl group used as an imidazole protection group of histidine is removed by thiophenol treatment. The formyl group used as an indole protection group of tryptophan is removed by acid treatment in the presence of the above 1,2-ethanedithiol, 1,4-butanedithiol or the like, and further it can be removed by alkali treatment with a diluted sodium hydroxide solution, diluted ammmonia or the like.

The protection of functional groups that should not participate in the reaction of starting materials and the protected groups, elimination of the protected groups, activation of the functional group that participate in the reaction or the like can be suitably selected from well-known groups and means. As the other methods for obtaining amides of proteins, for example, an α-carboxyl group of carboxy endgroup amino acid is protected by amidation, a peptide chain (protein) is elongated to the desired chain length at the side of the amino chain, a protein that the protected group of the α-amino group at the N-end of the peptide chain is eliminated and a protein that the protected group of the carboxyl group at the C-end of the peptide are produced, and the both peptide are condensed in a mixture solution as described above. The particular of the condensation reaction is as mentioned in the above. The protected protein obtained by the condensation is purified, all protected groups are removed by the above method, and crude protein can be obtained. The crude protein is purified by using a known purification means, main fructions are lyophilized and an desired amide of the protein can be obtained. For obtaining esters of the protein, for example, α-carboxyl groups of carboxy-end amino acids are condensed with desired alcohols to obtain amino acid esters, the esters are treated as shown in amides of the protein, and desired esters of the protein can be obtained.

The partial peptide or the salts of this invention can be produced by well-known methods for synthesizing peptides or by cutting the protein of this invention with a suitable peptidase. As the method for synthesizing the peptide, for example, a solid-phase synthesis mathod or liquid-phase synthesis method can be used. Namely, a partial peptide able to constitute the partial peptide of this invention or an amino acid is condensed with the remaining parts, when the product has a protected group, the protected group is eliminated, and the desired peptide can be produced.

As well-known condensation methods and the elimination of the protected groups, for example, the following methods are exemplified. M. Bodanszky and M. A. Ondetti, Peptide Synthesis, Interscience Publishers, New York (1966); Schroeder and Luebke, The Peptide, Academic Press, New York (1965); Nobuo Izumiya et al., Fundament and Experiments of Peptide Synthesis, Maruzen Co., (1975); Haruaki Yajima and Shunpei Sakakibara, Biochemical Experiment Lectures 1, Chemistry of Proteins IV, 205 (1977); Haruaki Yajima supervised, Continued Development of Medicines, Vol. 14, Peptide Synthesis, Hirokawa Shoten. After the reaction, further, the partial peptide of this invention can be purified by usual purification methods, for example, solvent extraction, distillation, column chromatography, liquid chromatography, recrystalization and their combination. When the partial peptide is obtained by the above methods, it can be changed into a suitable salt by a known method or the similar method. When a salt of the partil peptide is obtained, it can be changed into a released compound or the other salt by a known method or the similar method.

As the DNA coding the protein of this invention, any compounds that a base sequence coding the above-mentioned protein of this invention is contained can be used. Further. a genome DNA, a genome DNA library, the above-mentioned cDNA derived from cells and tissues, the above-mentioned cDNA library derived from cells and tissues, or synthetic DNA can be used. A vector used in the library can be selected from any one of bacteriophage, plasmid, cosmid, phagemid and the like. Using a total RNA or mRNA fruction prepred from the above cells or tissues, it can be directly amplified by Reverse Transcriptase Polymerase Chain Reaction (called as a RT-PCR method hereinafter). As the DNA coding the protein of this invention, any one of the following DNAs can be exemplified: for example, a DNA containing a base sequence represented by SEQ ID No.2, or a DNA, which has a base sequence hybridizing with a base sequence represented by SEQ ID No.2 under highstringent conditions and codes the protein having substantially the same activity as the protein of this invention (for example, citotoxin activity).

Further embodying, As the DNA coding a protein having the amino acid sequence represented by SEQ ID No. 1, the DNA having the base sequence represented by SEQ ID No. 2 can be used.

As the DNA coding the partial peptide of this invention, any one of DNAs containing the above base sequence coding the partial peptide of this invention can be used. Further. a genome DNA, a genome DNA library, the above-mentioned cDNA derived from cells and tissues, the above-mentioned cDNA library derived from cells and tissues, or synthetic DNA can be used. As the DNA coding the partial peptide of this invention, for example, any one of the following DNAs can be exemplified: for example, a DNA having a partial sequence of DNA having a base sequence represented by SEQ ID No.2, or a DNA having a prtial sequence of DNA, which has a base sequence hybridizing with a base sequence represented by SEQ ID No.2 under highstringent conditions and codes the protein having substantially the same activity as the protein of this invention (for example, citotoxin activity).

As cloning methods of the DNA perfectly coding the protein of this invention or the partial peptide (hereinafter, in the description of the cloning and expression of the DNA coding these protein and the like, case by case, these protein and the like is shorten as the protein of this invention), using a synthesized DNA primer having the partial base sequence of the protein of this invention, it is amplified by a known PCR method, or the DNA combined in a suitable vector is selected by hybridization with a DNA fraction or a synthesized DNA that codes a part or all region of the protein of this invention. The hybridization method can be conducted by the description of, for example, Molecular Cloning, $2^{nd}$, J. Sambrook et al., Cold Spring Harbor Lab. Press (1989). When a commertially available liblary is used, it can be conducted by the method described in an attached explanation. In the change of DNAbase sequences, using a known kit such as MutanTM-G (produced by Takara Shuzou Co.), MutanTM-K (produced by Takara Shuzou Co.) or the like, a Gapped duplex method, a Kunkel method, well-known methods or similar methods can be conducted. The DNA coding a cloned protein can be used as it is, or by digesting with a restriction enzyme as desired, or by addition of a linker. The DNA may have ATG, GTG or TTG as a translation initiation codon at the 5' end side and TAA, TGA or TAG as a translation termination codon at the 3' end side. The translation initiation codon and the translation termination codon can be added by using a suitable synthetic DNA adapter. The expression vector of the protein of this invention can be produced, for example, by means (i) that an desired DNA is cutt off from the DNA coding the protein of this invention, and (ii) that the DNA fraction is bonded to the downstream of the promoter in a suitable expression vector.

As the vector, a plasmid derived from *Echerichia coli* (such as pBR322, pBR325, pUC12, pUC13 or pET30), a plasmid derived from *Bacillus subtilis* (such as pUB110, pTP5 or pC194), a plasmid (such as pSH19, pSH15), bacteriophage derived from yeast, a bacteriophage such as λ phage, an animal virus such as a retro virus, a vaccinia virus, a Baculo virus or the like, pA1-11, pXT1, pRc/CMV, pRc/RSV or pcDNAI/Neo can be used. As the promoter used in this invention, any promoters suitable for the host used in the expression of genes can be used. For example, when animal cells are used as the host, a SR α promoter, SV40 early promoter, HIV•LTR promoter, CMV promoter or HSV-TK promoter can be exemplified. In these promoters, the CMV (cytomegalovirus) promoter, SR α promoter can be preferably used. When the host is an *Echerichia* family fungus, a trp promoter, lac promoter, recA promoter, A PL promoter, lpp promoter or T7 promoter is preferred. When the host is a *Bacillus* family fungus, a SPO1 promoter, SPO2 promoter or penP promoter is preferred. When the host is yeast, a PHO5 promoter, PGK promoter, GAP promoter or ADH promoter is preferred. When the host is an insect cell, a polyhedrin promoter, P10 promoter or the like preferred.

As the expression vectors other than the above vectors, if desired, vectors containing an enhancer, a selection marker, SV40 replication origin (occationally abbreviated as SV40ori hereinafter) or the like can be used. As the selection marker, for example, a dihydro folic acid reduction enzyme (occationally abbreviated as dhfr hereinafter) gene (methotrxate (MTX) resistance), an ampicillin resistance gene (occationally abbreviated as Ampr hereinafter), a neomycin resistance gene (occationally abbreviated as Neor hereinafter) G418 resistance and kanamycin resistance gene can be exemplified. Particularly, when the dhfr gene is used as a selection marker by using Chinese hamster cells defective a dhfr gene, combinant cells can be selected by a medium not containing thymidine. If necessary, further, a signal sequence fitted to the host is added to N end sides of the protein of this invention. When the host is an *Echerichia* family fungus, a PhoA signal sequence, OmpA signal sequence or the like can be used. When the host is a *Bacillus* family fungus, an α-amylase signal sequence, a subtilicin signal sequence or the like can be used. When the host is yeast, an MF α signal sequence, a SUC2 signal sequence, a SUC2 signal sequence or the like can be used. When the host is an animal cell, an insulin signal sequence, an α-interferon siganl sequence, an antibody molecular signal sequence or the like can be used. Using a vector containing the DNA coding such constructed protein of this invention, a transformant can be produced.

As the host, for example, an Genus *Echerichia*, a Genus *Bacillus*, yeast, insect cells, insects, animal cells or the like can be used. As an embodiment of Genus *Echerichia*, for example, *Escherichia coli* K12, DH1, DH5α (Proc. Natl. Acad. Sci. USA, Vol. 60, 160(1968)), JM103 (Nucleic Acids Research, Vol. 9, 309(1981)), JA221 (Journal of Molecular Biology, Vol. 120, 517(1978)), HB101 (Journal of Molecular Biology, Vol. 41, 459(1969)), C600 (Genetics, Vol. 39, 440(1954)) or the like can be used. As Genus *Bacillus*, for example, *Bacillus subtilis* MI114 (Gene, Vol. 24, 255(1983), 207-21 (Journal of Biochemistry, Vol. 95, 87(1984)) or the like can be used. As the yeast, for example, *Saccharomyces cerevisiae* AH22, AH22R, NA87-11A, DKD-5D, 20B-12, *Schizosaccharomyces pombe* NCYC1913, NCYC2036, *Pichia pastoris* KM71 or the like can be used.

As the insect cells, for example, when the virus is AcNPV, *Spodoptera frugiperda* cell; Sf cells, MG1 cells derived from midintestine of *Trichoplusia ni*, High Five TM cells derived from the egg of *Trichoplusia ni*, cells derived from *Mamestra brassicae*, cells derived from *Estigmena acrea* or the like can be used. When the virus is BmNPV, *Bombyx mori* N cells; BmN cells or the like can be used. As the Sf cells, for example, Sf9 cells (ATCC CRL1711), Sf21 cells (Vaughn, J. L. et al., In Vivo, 13, 213-217(1977)) or the like can be used. As the insects, for example, larvae of silkworms can be used (Maeda et al, Nature, Vol. 315, 592(1985)). As the animal cells, for example, monkey cell COS-7, Vero, chinese hamster cell CHO (abbreviated as a CHO cell hereinafter), dhfr gene defective chainese hamstercell CHO (abbreviated as a CHO(dhfr-) cell hereinafter), mouse L cells, mouse AtT-20, mouse myeloma cells, rat GH3, human FL cells or the like can be used. Moreover, several kinds of normal human cells, for example, liver cells, splenocytes, nerve cells, neuroglia, spleen β cells, bone marrow cells, mesangium cells, Langerhans cells, skin cells, epithelium cells, endothelium, fibroblast, fibrocells, muscle cells, fat cells, immunological cells (for example, macrophages, T cells, B cells, natural killer cells, mast cells, neutrophils, basophils, eosinophils, monocytes), megakaryocytes, synovial cells, cartilages, bone cells, osteoblasts, osteclasts, mammary grand cells, hepatic cells, interstitial cells, or precursor cells, stem cells or cancer cells of these cells can be used. For the transformation of Genus *Echerichia*, for example, it can be conducted by the method described in Proc. Natl. Acad. Sci. USA, Vol. 69, 2110(1972), Gene, Vol. 17, 107(1982) or the like.

For the transformation of Genus *Bacillus*, for example, it can be conducted by the method described in Molecular & General Genetics, Vol. 168, 111(1979) or the like. For the transformation of yeast, for example, it can be conducted by the method described in Methods in Enzymology, Vol. 194, 182-187(1991), Proc. Natl. Acad. Sci. USA, Vol. 75, 1929 (1978) or the like. For the transformation of insect cells or insects, for example, it can be conducted by the method described in Bio/Technology, 6, 47-55(1988) or the like.

For the transformation of animal cells, for example, it can be conducted by the method described in Cell Engineering, separate volume 8, New Cell engineering Experiment protocol, 263-267(1995), published by Shujunsha, and Virology, Vol. 52, 456 (1973). Using the above methods, transformants, which are transformed with expression vectors containing DNA coding the protein, can be obtained. When the transformants that the hosts are Genus *Echerichia* or Genus *Bacillus* are cultured, a liquid medium is suitable as the medium used in the culture. In the medium, carbon sources, nitrogen sources, inorganic and the like, which are necessary for the growing of the transformants, are contained. As the carbon sources, for example, glucose, dexitrin, soluble starch, succrose or the like can be exemplified. As the nitrogen sources, for example, inorganic or organic materials such as ammonium salts, nitrates, corn steep liquor, peptone, casein, meat extract, bean cakes, potato extract and the like can be used. As the inorganic materials, for example, calcium chloride, monosodium phosphate and magnesium chloride can be exemplified. Yeast extract, vitamines, growth-stimulating materials or the like can be added. About pH 5-8 of the medium is preferably used.

As the medium for culturing Genus *Escherichia*, for example, a M9 medium containing glucose and casamino acid (Miller, Journal of Experiments in Molecular Genetics, 431-433, Cold Spring Harbor Laboratory, New York 1972) is preferred. If necessary, for efficient action of the promoter, for example, an agent such as 3β-indolyl acrylic acid can be added. When the host is Genus *Escherichia*, the culture is usually concducted at a temperature of about 15~43° C. for about 31~24 hours, if necessary, aeration or stirring can be added. When the host is *Bacillus* family fungi, the culture is usually conducted at a temperature of about 30~40° C. for about 6~24 hous, if necessary, aeration or stirring can be added.

When the transformant that the host is yeast is cultured, as the medium, for example, a Burkholder minimal medium (Bostian, K. L. et al., Proc. Natl. Acad. Sci. USA, Vol. 77, 4505(1980)) or a SD medium containing 0.5% casamino acid (Bitter, G. A. et al., Proc. Natl. Acad. Sci. USA, Vol. 81, 5330(1984)) can be exemplified. About pH 5-8 of the medium is preferably used. The culture is usually conducted at a temperature of about 20~35° C. for about 24~72 hours, if necessary, aeration or stirring can be added. When the transformant that the host is an insect cell or an insect is cultured, as the medium, Grace's Insect Medium (Grace, T. C. C., Nature, 195,788(1962)) can be used by suitably adding an addition of immobilized 10% bovine serum or the like. About pH 6.2-5.4 of the medium is preferably used. The culture is usually conducted at a temperature of about 27° C. for about 3~5 days, if necessary, aeration or stirring can be added. When the transformant that the host is an animal cell, as the medium, for example, a MEM medium containing about 5~20% fetus bovine serum (Science, Vol. 122, 501(1952)), a D M E M medium (Virology, Vol. 8, 396(1959)), an RPMI 1640 medium (The Jounal of the American Medical Association, Vol. 199, 519(1967)), a 199 medium (Proceeding of the Society for the Biological Medicine, Vol. 73,1(1950)) or the like can be used. About pH 6-8 of the medium is preferably used. The culture is usually conducted at a temperature of about 30~40° C. for about 15~60 hours, if necessary, aeration or stirring can be added. As descrived in the above, the protein of this invention can be produced out of the cells of the transformants.

For separation and purification of the protein of theis invention, for example, the following methods can be suitably used. When the protein of this invention is extracted from the cultured fungi or cells, after the culture, the fungi or cells are collected by a well-known method, suspended in a suitable buffer, and destroyed by ultrasound, lysozyme and/or freze-thawing or the like. Then, the crude extracted liquid of the protein is obtained by centrifugation or filtration. A protein denaturant such as urea or guanidine hydrochloride, or a surface-active agent such as tritonX-100TM can be contained in the buffer. When the protein is secreted in the medium liquid, after the culture is finished, the fungi or cells and supernatant are separated by a well-known method, and the supernatant is collected. Such obtained culture supernatant or the protein contained in the extracted liquid is purified by a combination of well-known separation and purification methods. These well-known separation and purification methods are methods using salting-out techniques or solubilities by a solvent precipitation method, a dialysis method, a method using a difference in the molecuar weight such as ultrafiltration and SDS-polyacrylamide gel electrophoresis or the like, a method using a difference of the charge such as ion exchange chromatography, a method using a difference of hydrophobic such as hydrophobic chromatography, a method using specific affinity such as afnity chromatography, a method using a difference of hydrophobic such as reverse phase high-speed liquid chromatography, a method using a difference of isoelectric points such as isoelectrcophoresis can be used.

When such a protein is obtained in the form of free, it can be converted into a salt by a well-known method or a similar method. On the other hand, when the protein is obtained in the form of a salt, it can be converted into a free form or the other salt by a well-known method or a similar method. The protein produced by a recombinant may be further reacted with a suitable protein modification enzyme before or after purifying the protein to optionally modify or partially remove the polypeptide. As the protein modification enzyme, for example, trypsin, chymotrypsin, arginylendopeptidase, protein kinase, glycosidase or the like may be used. The activitis of such obtained protein of this invention or salts thereof may be determined by a bond experiment with a labeled ligand and enzyme immunoassay using a specific antibody or the like.

The antibodies for the protein, the partial peptide or the salts of this invention, may be a polyclonal antibody or monoclonal antibody on condition that the antibodies can recognize the protein, the partial peptide and the salts. The antibodies for the protein, the partial peptide or the salts of this invention (in the following description of antibodies, these protein and the like may be abbreviated as the protein of this invention) may be produced by using the protein as the antigen and by a well-known production method of antibodies or anti-serum.

Production of a Monoclonal Antibody (a) Production of cells of monoclonal antibody production:
The protein of this invention is administered to a warm-blodded animal at a position, which can produce an antibody by the administration, with itself or a carrier or a diluent. In the administration, to enhance the effect of antibody production, a complete Freund's adjuvant or an incomplete Freund's adjuvant may be administered. The administration is usually conducted once for each 2~6 weeks, and total is 2~10 times. The warm-blooded animals are, for example, monkeys, rabbits, dogs, guinea pigs, mice, rats, sheep, goats, chickens and the like, preferably mice and rats. At the production of cells for producing a monoclonal antibody, the warm-blooded animal immunized with an antigen, for example, mice are used. A mouse recognizable an antibody value is selected from the mice, the spleen or the lymph is collected after 2~5 days of the final immunization, and the cells of monoclonal antibody production contained in the spleen or the lymph are fused with myeloma cells of the same kind or different kind of animals to prepare a hybridoma for producing a monoclonal antibody. The antibody value in the antiserum may be determined, for example, by a method that the antiserum is reacted with an after-mentioned labeled protein, and the activity of the labeled agent bound to the antibody is measured. The fusion operation may be conducted by a known method such as a method of Kohler and Milstein (Nature, 256, 495 (1975)). As the fusion promotion agent, for example, polyethylene glycol (PEG), a Sendai virus or the like, preferably PEG may be used.

As the myeloma, for example, myloma celles of warm-blooded animals such as NS-1, P3U1, SP2/0, AP-1 and AP-1, preferably P3U1 can be exemplified. The preferabl ratio of the number of the antibody production cells (spleen cells) to the number of myeloma cells is around 1:1~20:1. PEG (preferably, PEG1000-PEG6000) is added in the concentration of around 10~80%, and incubation is conducted at a temperature of 20~40° C., preferably 30~37° C. for 1~10 minutes, and cell fusion is efficiently performed. In screening of a hybridoma of monoclonal antibody production, several kinds of methods can be used, for example, there are a method that a supernatant of hyblidoma culture is added to a solid phase (such as a micro plate) adsorbing a protein antigen directly or with a carrier, and an anti-immunoglobulin antibody, which is labeled with a radioactive material or an enzyme yeast, (when the cells for using in cell fusion is a mouse, an anti-mouse immunoglobulin is used) or a protein A is added so as to detect the monoclonal antibody bound to the solid phase; and a method that a supernatant of hyblidoma culture is added to a solid phase adsorbing an anti-immunoglobulin antibody or a protein A, a protein labeling a radioactive material or an enzyme yeast is added, and the monoclonal antibody bound to the solid phase is detected. The selection of the monoclonal antibody may be conducted by a known method or a similar method thereof. Usually, it may be conducted by a medium for animal cells that HAT (hypoxanthine, amino pterin, thymidine) is added. As the medium for selection and breeding, any medium that the hyblidoma can breed may be used. As an example, a RPMI 1640 medium containing 1~20%, preferably 10~20% bovine fetus serum, a GIT medium containing 1~10% bovine fetus serum (produced by Wako Junyaku Kougyou Co.) or a medium not containing serum for hybridoma culture (SFM-101, Nissui Seiyaku Co.) may be used. The culture temperature is usually 20~40° C., preferably about 37° C. The culture time is usually 5 days~3 weeks, preferably 1 week~2 weeks. The culture may be usually conducted in a 5% carbon dioxide. The antibody value of the supernatant of hyblidoma culture can be determined as shown in the above-mentioned method for measuring the antibody value in the antiserum.

(b) Purification of the monoclonal antibody: The separation and purification of the monoclonal antibody may be conducted by a known method, for example, a separation and purification method for immunogloblins (such as a salting-out method, an alcohol precipitation method, a isoelectric precipitation method, an electrophoresis method, a adsorption and desorption method with an ion-exchanger (for example, DEAE), a ultracentrifuge method, a gel filtration method, or a specific purification method that only an antibody is cllected with an active absorbant such as an antigen-binding solid phase or protein A or protein G, and the bond is released to obtain the antibody).

[Production of the Polyclonal Antibody]

The polyclonal antibody of this invention can be produced by a known method or a similar method. As an example, using an immunoanigen (protein antigen) itself or a complex of the immunoantigen and a carrier protein, it immunizes to a warm-blooded animal by using the same method as in the above-mentioed method for producing a monoclonal antibody, materials containing the antibody for the protein of this invention are collected, and the antibody is separated and purified. As to the complex of an immunoantigen for immunizing a warm-blooded animal and a carrier protein, the kind of the carrier protein and a mixture ratio of the carrier to a hapten are not important, on condition that the antibody can be efficiently produced for the hapten immunized by closslinking with the carrier. For example, the bovine serum albumin, bovine cyclogloblin, hemocyanin or the like can be used for coupling with the hapten at a weight ratio of about 0.1~20, preferably about 1~5 to 1 of hapten. In the coupling of the hapten and the carrier, several kinds of condensation agents such as active ester agents containing glutaraldehyde, carbodiimide, maleimid active ester, a thiol group and a dithiopyridyl group can be used. The products from the condensation are administered to the parts of warm-blooded animals able to produce the antibody, along with itself or a carrier or a diluent. To enhance the ability of antibody production at the administration, a complete Freund's adjuvant or incomplete Freund's adjuvant may be administered. The administration is usually conducted once for every 2~6 weeks, and total is about 3~10 times. The polyclonal antibody can be collected from blood, ascites, preferably blood of the warm-blooded animal immunized by the above method. The polyclonal antibody value in the antiserum is determined by the same method described in the above determination of the antibody value in the antiserum. The separation and purification of the polyclonal antibody can be conducted by the same method of separation and purification of immunogloblin as in that of the above separation and purification of the monoclonal antibody.

The treating agents containing the protein or the partial peptide of this invention and the protein of this invention and the like have cancer cytotoxic activity, so that the agents may be used as agents for extracting disease tissues (the extract contains all and partial, preferably partial extract), and particularly, for treating fixed cancer. When the protein of this invention and the like is used as the above treating and preventing agents, it is used after it is purified to at least 90%, preferably 95% or more, more preferably 98% or more, and further preferably 99% or more.

The inhibition activity of cancer cell proliferation of the protein of this invention or the like can be determined by a known method, or a cytotoxin activity or an activity causing cell death is determined by known method or a similar method, preferably by the method described in the after-mentioed experiments. As the test compounds, for example, peptides, proteins, non-peptide compounds, synthetic compounds, fermentation products, cell extract, plant extract, animal tissue extract and blood plasma can be exemplified. These compounds may be new compounds or known compounds.

The compounds or the salts obtained by the screening method or the kit for screening of this invention are selected from the above test compounds, for example, peptides, proteins, non-peptide compounds, synthetic compounds, fermentation products, cell extract, plant extract, animal tissue extract and blood plasma. These compounds have an activity inhibiting the cytotoxic activity of the protein of this invention or the like or the inhibition activity of cancer cell proliferation of the protein of this invention or the like. As the salts of the compounds, the salts similar to the salts of the protein of this invention can be used.

When the compounds obtained by using the screening method or the kit for screening are used as the above treating agents, they can be used by usual means. For example, they are used as tablets, capsules, elixirs, microcapsules, sterile solutions, suspension or the like. As such obtained pharmaceutical preparations are safety and have low toxicity, for example, they may be administered to a human or a warm-blooded animal (such as mice, rats, rabbits, goats, pigs, cows, horses, birds, cats, dogs, monkeys and the like). The dosage weights of the compounds or salts thereof are changed by the action, the disease, the dosage route or the like. Commonly, in adults (estimated at 60 kg weight), about 0.1~100 mg of the compound per day, preferably about 1.0~50 mg, more preferbly about 1.0~20 mg can be administered. In parenteral administration, the dosage of the compounds that is variable by the object, the disease and the like, usually in adults (estimated at 60 kg weight), is suitably about 0.01~30 mg of the compound per day, more preferably about 0.1~20 mg, further preferably about 0.1~10 mg by intravenous injection. In the other animals, the dosage of the weight estimated at 60 kg can be used.

Screening of the candidate compounds of medicine for diseases: Since the protein or the like of this invention have a cytotoxic activity, the compounds or the salts promoting the function (such as a cytotoxic activity) of the protein or the like of this invention, for example, may be used as agents for treating cancers. On the other hand, the salts inhibiting the function of the protein or the like of this invention, for example, may be used as agents for treating and preventing gastritis and gastric ulcer. Accordingly, the protein or the like of this invention are effectively used as reagents for screening the compounds or the salts that promote or inhibit the function of the protein or the like of this invention.

Namely, this invention provides (1) a screening method characterized in that the protein or the partial peptide or the salts of this invention are used, and the method screens the compounds promoting the function (such as a cytotoxic activity) of the protein or the partial peptide or the salts of this invention, or the method screens the compounds inhibiting the function (such as a cytotoxic activity) of the protein or the partial peptide or the salts of this invention. The compounds promoting the function may be abbriviated as 'promoters' and the compounds inhibiting the function is abbreviated as 'inhibitors' hereinafter.

Moreover, this invention provides (2) a kit for screening promoters or inhibitors, characterized in that the protein or the prtial peptide or the salts of this invention are contained. The above kit may be abbreviated as 'a kit for screening of this invention' hereinafter.

In embodiment, for example, in the above (1), it provides a screening method of promoters or inhibitors, characterixed in that comparison is conducted between case (i) and case (ii). The case (i) is that the protein or the partial peptide or the salts of this invention are contacted with a cell, which is a normal cell containing a blood cell derived from a tissue of the above warm-blooded animals (preferably human) or the above-mentioned cancer cell. The case (ii) is that the protein or the partial peptide or the salts of this invention are contacted with a cell, which is a normal cell containing a blood cell derived from a tissue of the above warm-blooded animals (preferably human) or the above-mentioned cancer cell, and a test compound.

In embodiment, further, in the above (2), it provides a kit for screening promoters or inhibitors, characterixed in that it contains the protein or the prtial peptide or the salts of this invention, and a cell that is a normal cell containing a blood cell derived from a tissue of the above warm-blooded animals (preferably human) or the above-mentioned cancer cell or the like.

Further, concretely, in the screening method, case (i) and case (ii) are characterized in that the cytotoxic activities of the protein and the like of this invention are determined and compared.

The cytotoxic activity, the cell multiplication inhibition activity, and the activity causing cell death of the protein or the like of this invention can be determined by a known method or a similar method. However, more concretely, using established cell lines and the like, further, a substrate containing the test compound, a negative control which is a substrate not containing the test compound, and a positive control which is a substrate containing M toxin, these three or two are used. Comparing the cell numbers under the conditions satisfyable in statistical significance, inhibition activity of the cytotoxic activity or the cell multiplication activity, or the specified sample having the inhibition activity of the cytotoxic activity or the cell multiplication activity can be detected by existence or absence of the activities or increase and decrease. The cells used in the detection method are, for example, normal cells containing a blood cell derived from a tissue of the above warm-blooded animals (preferably human) or the above-mentioned cancer cells of several kinds of warm-blooded animals (for example, cancer of the endometrium, endometrioma, breast cancer, cancer of the stomach, hepatic carcinoma, spleen cancer, carcinoma of the galbladder, colon cancer, prostatic cancer, lung cancer, renal cancer, neuroblastoma, cancer of the urinary bladder, malignant melanoma, cancer of the tongue, carcinoma of the gingiva, mouse fibroblast, African green monkey kidneys rat liver cancer, and the like).

As the test compunds, for example, peptides, proteins, non-peptide compounds, synthetic compounds, fermentation products, cell extracts, plant extracts, animal tissue extracts and the like can be exemplified. These compounds may be new compounds or known compounds. For conducting the above screening method, the protein or the like of this invention is suspended in buffer suitable to the screening, and the samples of the protein or the like of this invention are prepared. As the buffer, phosphate buffer of pH about 4~10 (preferably, pH about 6~8), Tris-hydrochloride buffer or the like, which does not inhibit the reaction of the protein or the like of this invention and the test compounds, may be used.

As concrete screening method, after the screening examination, ① a method for directly observing the cell changes under a microscope and counting the cells with a hemocytometer or the like, ② a method that the change of potassium, hemoglobins and the like, which are eluted from cells by the cell dath, is catched, ③ a method for determining the remaining cells after the reaction with tetrazolium salts or the like, ④ a method for determining the remining living cells with a radioactive labelled subsatance, ⑤ a method for confirming the cell death by induction of cell apoptosis and the like can be exemplified. For example, as a compound increasing the cytotoxic activity of the protein or the like of this invention, a test compound in which the cytotoxic activity in the above case (ii) compared with the above case (i) is increased by about 20% or more, more preferably 30% or more, further preferably 50% or more, can be selected. On the other hand, as a compound inhibiting the cytotoxic activity of the protein or the like of this invention, a test compound in which the cytotoxic activity in the above case (ii) compared with the above case (i) is inhibited by about 20% or more, more preferably 30% or more, further preferably 50% or more, can be selected. These may be conducted as a method for high throughput screening. In the following, as method ②, a method for determining hemoglobins by hemolytic reaction and as method ③, a WST method are respectively used. In the methods, active carbon, CM cellulose and calcium alginate are selected as adsorbents which show the anti-M toxin activity.

It is further possible to examine and compare the solutions containing these anion control, positive control and test compounds with animal models to confirm the effects of the animal levels of the anti-M toxic materials. In these cases, many kinds of warm-blooded animals may be used. Particularly, a mouse, a rat, a dog, and a monkey may be used. As infected models, a Mongolian gerbil, a mouse and a monkey are effectively used.

When the compounds obtained by the screening method or the kit for screening of this invention are used as the above treating and preventing agents, these compounds can be used by usual means. For example, using the same methods of the pharmaceutical preparations of the protein of the invention, they are used as tablets, capsules, elixirs, microcapsules, sterile solutions, suspension or the like. As such obtained preparations are safety and have low toxicity, for example, they may be administered to a human or a warm-blooded animal (such as a mouse, a rat, a rabbit, a goat, a pig, a cow, a horse, a bird, a cat, a dog, a monkey and the like). The dosage weights of the compounds or salts thereof are changed by the action, the disease, the dosage route or the like. When the compounds are used for increasing the function of the protein or the like of this invention as a tissue regeneration agent after removing the disease tissues, commonly, in adults (estimated at 60 kg weight), about 0.1~100 mg of the compound per day, preferably about 1.0~50 mg, more preferbly about 1.0~20 mg can be orally administered. For the other animals, the dosage of the weight estimated at 60 kg can be used.

Quantification of the protein or the partial peptide or the salts of this invention:

The antibodies for the protein and the like of this invention (occasionally, abbreviated as the antibodies of this invention, hereinafter) can specifically recognize the protein and the like of this invention, so that they can be used for quantification of the protein and the like of this invention in test liquid, particularly, quantification by a sandwich immunization technique. Namely, this invention provides (i) a method for quantifying the protein and the like of this invention in test liquid, characterized in that the antibody of this invention and test liquid and the protein and the like of this invention are conpetitively reacted, the ratios of the labelled protein and the like of this invention that bind to the antibody are determined, and (ii) a method for quantifying the protein and the like of this invention in test liquid, characterized in that the test liquid and the antibody insolubilized on a carrier and the other labelled antibody of this invention are reacted at the same time or continuously, and then the activity of the labeling agent on the insolubilized carrier is determined. In the above quantitative method (ii), preferably, one antibody is an antibody recognizing the N ends of the protein and the like of this invention, the other antibody is an antibody reacting with the C ends of the protein and the like of this invention.

Moreover, using a monoclonal antibody for the protein and the like of this invention (ocasionally abbreviated as a monoclonal antibody of this invention, hereinafter), the quantification of the protein and the like of this invention can be conducted, and further, the detection can be conducted by using tissue dyeing. As these objects, antibody moleculars themselves may be used, or F(ab')2, Fab', or Fab fraction of antibody moleculars may be used. The quantification of the protein and the like of this invention using of this invention should not be limited. For example, the quantity of the antibody, antigen or antibody-antigen complex corresponding to the quantity of the antigen (for example, the quantity of the protein) in the test liquid is chemically or physically detected, the obtained quantity is determined by a standard curve that is formed by standard liquid containing the antigen of a known quantity. As examples, nephelometry, a competition method, an immunometric method, and a sandwich method are preferably usable. Considering sensitivity and specificity, the after-mentioned sandwich method is preferred. As the labelling agents used in a determination method with a labelled substance, for example, a radioactive isotope, enzyme, fluorescence substance, luminescent substance and the like are exemplified. As the adioactive isotope, for example, 〔$^{125}$ I〕, 〔$^{131}$I〕, 〔$^{3}$H〕, 〔$^{14}$C 〕may be used. As the enzyme, stable and high active isotopes, for example, β-galactosidase, β-glucosidase, alkaliphosphatase, peroxidase, a dehydrogenase of malic acid and the like may be used. As the fluorescence substance, for example, fluorescamine, fluorescein isothiocyanate and the like may be used. As the luminescent substance, for example, luminol, luminol derivatives, luciferin, lucigenin and the like may be used. Moreover, for the bind of an antibody or an antigen and a labelling agent, a biotin-avidin type may be used.

The insolubilization of an antigen or an antibody may be conducted by physical adsorption, or the chemical bonding usually used for the insolubilization of proteins or enzymes. As the carrier, insoluble polysaccharides such as agarose, dextran and cellulose, synthetic resins such as polystyrene, polyacrylamide and silicone or glass can be exemplified. In the sandwich method, the test liquid is reacted with the insolubilized monoclonal antibody of this invention (primary reaction), then it is reacted with the other labelled monoclonal antibody of this inevention (secondary reaction), and the activity of the labelling agent on the insolubilized carrier is determined to determine the quantity of the protein of this invention in the test liquid. The primary reaction and the secondary reaction can be changed. Otherwise these reactions may be conducted at the same time or by sliding the starting times. The labelling agent and the isolubilizing method may be treated the same as these reactions. In the immuno assay by using the sandwich method, it is unnecessary that the antibody used as an antibody for a solid phase or an antibody for labelling is one kind. A mixture of two or more kinds of antibodies may be used for improving the determination sensitivity. In the determination method of the protein and the like of this invention by using the sandwich method of this invention, the monoclonal antibodies used in the primary reaction and the secondary reaction preferably have different parts that the protein and the like of this invention is bound. Namely, as to the antibodies used in the primary reaction and the secondary reaction, for example, when the antibody used in the secondary reaction recognaize the C end of the protein and the like of this invention, the antibody used in the primary reaction preferably recognize a part except the C end, for example, the N end.

The monoclonal antibody of this invention may be used in a determination system except the sandwich method such as a competition method, or an immunometric method or nephelometry. In the competition method, antigens and labelled antigens in test liquid are competitively reacted with antibodies, and then unreacted labelled antibodies (F) and labelled antigens (B) bound to the antibodies are separated (B/F separation), the labelled quantity of B or F is determined, and the antigen quantity is quantified. In the reaction method, soluble antibodies are used as antibodies. In the B/F separation, a liquid phase method that polyethyleneglycol or the second antibody for the above antibody is used, and a solid phase method that a solid phase antibody is used as the first antibody, or a soluble antibody is used as the first antibody and a solid phase antibody is used as the second antibody are exemplified. In the immunometric method, the antigens and the solid phase antigens in the test liquid are competitively reacted with labelled antibodies of a definite amount and then the solid phase and the liquid pahse are separated. Otherwise, the antigens in the test liquid and the labelled antibodies of an excess amount are reacted, the solid phase antibodies are added to bind the unreacted labelled antibodies to the solid phase, and the solid phase and the liquid phase are separated. Continuously, the labelled quantity of any one of the both phases is determined, and the antigen quantity in the test liquid is determined. In the nephelometry, the quantity of unsoluble precipitates occured as the result of the antigen-antibody reaction in the gel or in the solution is determained. When the quantity of antigens in the test liquid is little and a small amount of precipitates are obtained, lasernephelometry using laser scattering and the like may be preferably used.

When these immunological determination methods are applied in the determination method of this invention, special conditions and establishment of operations are unnecessary Adding common technical ideas in the fields to usual conditions and operation methods in each method, the determination systems of the protein and the like of this invention may be constructed. As to the details of these common technical means, general books, specialized books may be referenced. For example, Kan Irie edited, Radioimmuno Assay, Kodan-sha (1974), Kan Irie edited, Radioimmuno Assay, continued, Kodan-sha (1979), Eiji Ishikawa et al. edited, Immunoenzymometric Assay, Igaku Shoin (1978), Eiji Ishikawa et al. edited, Immunoenzymometric Assay, $2^{nd}$ edition, Igaku Shoin (1982), Eiji Ishikawa et al. edited, Immunoenzymometric Assay, 3rd edition, Igaku Shoin (1987), Methods in ENZYMOLOGY, Vol. 70, Immunochemical Techniques (Part A): ibid., Vol. 73, Immunochemical Techniques (Part B), ibid., Vol. 74, Immunochemical Techniques (Part C), ibid., Vol. 84 (Immunochemical Techniques (Part D: Selected Immunoassays), ibid., Vol. 92 (Immunochemical Techniques (Part E: Monoclonal Antibodies and General Immunoassay Methods), ibid., Vol. 121 (Immunochemical Techniques (Part I: Hybridoma Technology and Monoclonal Antibodies), all are published by Academic Press Co. can be referenced. As described above, by using the antibody of this invention, the protein and the like of this invention can be sensitively quantified. Moreover, by quantifying the concentrations of the protein and the like of this invention by using the antibody of this invention, when the incresed concentrations of the protein and the like of this invention are detected in patients of Helicobacter pylori infection, patients have diseases, for example, gastritis, gastric ulcer, gastric cancer, valvular disease, diabetes mellitus, various cancers (such as cancer of the endometrium, endometrioma, breast cancer, colon cancer, prostatic cancer, lung cancer, hepatic carcinoma, spleen cancer, carcinoma of the galbladder, renal cancer, neuroblastoma, cancer of the bladdar, malignant melanoma and the like). Otherwise, it is possible to diagnose that the possibility of future morbidity is high. The antibody of this invention can be used for detection of the protein and the like of this invention in test liquid such as body fluid or tissues. It is used for formation of the antibody column for using purifying the protein and the like of this invention, detection of the protein and the like of this invention in each fraction at the purification, and analysis of the behavior of the protein and the like of this invention in test cells.

The medicine containing the antibody of this invention, the antibody of this invention (neutralizing antibody) having an action for neutralizing the activities of the protein and the like of this invention can be used as medicines for treating and preventing diseases such as gastritis, gastric ulcer, gastric cancer, valvular disease, diabetes mellitus, various cancers (such as cancer of the endometrium, endometrioma, breast cancer, colon cancer, prostatic cancer, lung cancer, renal carcinoma, neuroblastoma, cancer of the bladder, malignant melanoma and the like). The humanized antibody of this invention for the protein and the like of this invention can be used as medicines for treating and preventing diseases such as gastritis, gastric ulcer, gastric cancer, valvular disease, diabetes mellitus, various cancers (such as cancer of the endometrium, endometrioma, breast cancer, colon cancer, prostatic cancer, lung cancer, renal carcinoma, neuroblastoma, cancer of the bladder, malignant melanoma and the like). The humanized antibody can be formed with reference to the methods described in Nat Biotechnol, 14, 845-851 (1996), Nat Genet. 15, 146-156 (1997) and PNAS, 97(2), 722-727 (2000). In the following, these neutralizing antibody and humanized antibody of this invention are abbreviated as the antibody of this invention.

The above treating and preventing agents containing the antibody of this invention can can be orally or parenterally administered as liquid as it is or a medicine composition of a suitable dosage form to human or mammalia (such as a mouse, a rabbit, a goat, a pig, a cow, a cat, a dog, a monkey and the like). The dosage of the agents is changed by the object, the disease, the condition of illness, the dosage route or the like. When the agents are used for treating or preventing a tumor of the endometrium, a dose of the antibody of this invention is usually 0.01~20 mg/kg weight, preferably 0.1~10 mg/kg weight, more preferably 0.1~5 mg/kg weight about 1-5 times per day, preferably about 1-3 times per day. It is conveniant to administer the agent by an intravenous injection. A dosage in the other parenteral or oral administration also may be according to the above dosage. When the condition of illness is very severe, the dosage may be increased in proportion to the condition. The antibody of this invention can be administered as it is or as a suitable medical composition. The medical composition used in the administration contains a pharmacologically allowable carrier for the above antibody or the salt, a diluent or an excipient. Such a composition may be provided as a dosage form suitable for oral or parenteral administration. Namely, for example, as the composition for oral administration, the dosage form is solid or liquid, concretely a tablet (containing a sugar-coated tablet and a film coated tablet), a pill, a granule, powder, a capsule (containing a soft capsule), syrup, emulsion, suspension or the like. Such a composition is prepared by a known method, and it may contain the carrier usually used, a diluent or an excipient. For example, as the carrier for the tablet and the excipient, lactose, starch, sucrose, magnesium stearate and the like can be used.

After-mentioned sequence numbers of the sequence listing show the following sequence.

SEQ ID No.1: it shows an amino acid sequence deribed from *Helicobacter pylori* 60190 (M toxin).

SEQ ID No.2: it shows a base sequence of DNA that codes derived from *Helicobacter pylori* 60190 protein (M toxin) of this invention having the amino acid sequence represented by SEQ ID No.1.

SEQ ID No.3: it shows a base sequence of the primer (synthetic) DNA used in Example 3.

SEQ ID No.4: it shows a base sequence of the primer (synthetic) DNA used in Example 3.

The transformant, *Escherichia coli* M toxin/pET30EK/LIC/DH5α obtained in after-mentioned Example 3 has been deposited by deposit No. FERM BP-8218 on 17 Oct. 2002 at the International Patent Organism Depository, National Institute of Advanced Industrial Science and Technology (IPOD), AAIST, Tsukuba Central 6, 1-1, Higashi 1-chome, Tsukuba City, Ibaraki Prefecture, 305-8516, Japan. Moreover, the hybridoma clone No. 4 obtained in after-mentioned Example 4 has been deposited by deposit No. FERM BP-8222 as BALB-c/P3U1/004-1G9 on 23 Oct. 2002 at the International Patent Organism Depository, National Institute of Advanced Industrial and Technology (IPOD). Further, the hybridoma clone No. 101 has been deposited by deposit No. FERM BP-8223 as BALB-c/P3U1/101-1C10 on 23 Oct. 2002 at the International Patent Organism Depository, National Institute of Advanced Industrial Science and Technology (IPOD) . The hybridoma clone No. 116 has been deposited by deposit No. FERM BP-8224 as BALB-c/P3U1/116-5D7 on 23 Oct. 2002 at the International Patent Organism Depository, National Institute of Advanced Industrial Science and Technology (IPOD).

EXAMPLES

This invention will be understood more readily in reference to the following examples. However, these examples are intended to illustrate this invention and are not to be construed to limit the scope of the invention. The gene manipulation using *E. coli* was according to the method described in Molecular Cloning.

Example 1

A Method for Purifying and Extracting the Toxin of this Invention from *Helicobacter pylori*

*Helicobacter pylori* can be obtained by a separated strain which has already established (for example, from American Type Culture Collection) or by culturing a strain separated from clinical test samples. In this example, a separated strain of *Helicobacter pylori* 60190 was used. Using an agar medium that 5% bovine serum (produced by Sigma Co.) was added to a Brain Heart Infusion agar medium (poduced by Difco Co.), this separated strain was subcultured in 2-5 passages for about 1-2 weeks at a temperature of 37° C. and a humidity of 90% or more under microaerobic conditions ($CO_2$ 5-10%). It was confirmed under a microscope that the cells were not died or not in a colloi form but grown satisfactorily. The cells were transferred to Brain Heart Infusion agar culture produced by Difco Co.) plate containing not serum but 5% 2,6-di-O-methyl-β-cyclodextrin. After the culture and grown conditions were confirmed under the same conditions as described in the above, the cells were transferred to cultures containing 2,6-di-O-methyl-β-cyclodextrin with gradual stepwise decreases, i.e., 2%, 1% and 0.5% of the concentration.

In a liquid culture of Brain Heart Infusion containing 0.5% 2,6-di-O-methyl-β-cyclodextrin, the cells were cultured at a temperature of 37° C. under microaerobic conditions for about 16 hours, while agitated with a rotary shaker at 100-120 rpm. Pelletal bacteria cells were collected in by centrifugation at 10000×g for 20 minutes. These were suspended in 10 mM Tris-HCl pH7.7 buffer (abbreviated as buffer A, hereinafter. The pH is fully 6.1 or more, because the pH of aimed protein is pI 6.08.) and sonicated. After storing overnight at a temperature of −80° C., the cells were sonicated again and centrifuged at 100000×g for 60 minutes. Only the most upper layer of separated three layers was extracted.

The extract liquid was crudely purified with a 70% solution of ammonium sulfat. The resulting extract was purified by ion exchange chromatography with anion exchange resin of beads having relatively big particle diameters (DEAE Sephacel of Amersham Pharmacia Biotech AB). The buffer A was used as equilibrium buffer, and a mixture of the buffer A and a solution of 0.3M NaCl salt was used as eluate. Using the buffer A and the eluate, the cells were extracted by concentration gradient. A suitable quantity of each fraction was added dropwise on wells that HeLa cells were seeded, and cell viability was evaluated in each well. The evaluation was conducted by using WST assay using Cell Counting kits (DOJIN Laboratories). Comparing with a control, fractions showing significantly less viability and fractions having relatively coinciding increase curves of the protein were evaluated along with the results of electrophoresis to use as sample fractions for the next purification process.

Hydrophobic chromatography (Phenyl Sepharose CL-4B, Amersham Pharmacia Biotech AB) that has a different separation system from that of the next time was selected. Equilibrium buffer containing 1M ammonium sulfate in 10 mM phosphate buffer was used. Elution buffer containing 40% ethylene glycol in 10 mM phosphate buffer was used. After the cells were extracted by concentration gradient, each sample was evaluated by the same method as described in the above.

The samples extracted by the above process were extracted again by anion exchange chromatography with beads having relatively small particle diameters (RESOURCE Q of Amersham Pharmacia Biotech AB). The buffer A was used as equilibrium buffer, and a mixture of the buffer A and a solution of 1M NaCl salt was used as elution buffer. Using the chromatography, a single band of protein of about 41000 of a molecular weight was finally obtained. The kind and order of these chromatographys may be changed and may be further added.

After the resulting signal band was stained with Coomassie Brilliant Blue, it was transcripted on a nitrocellulose membrane or (polyvinylidene difluoride) membrane with a blotting apparatus and analyzed with an amino acid sequencer. As the results, as described in the above, the amino acid sequences of N ends of gene locus HP1037 of a registered database (*Helicobacter pylori* 22695) matched with 95% (19 bases in 20 bases). (FIG. 1)

Example 2

Amino Acid Sequences and DNA Sequences by a Gene Technological Production Method In this example, a separation strain of *Helicobacter pylori* 60190 was used. As described in the above, all gene analyses of *Helicobacter pylori* 22695 of different strains were already done. Homologous gene locus can be estimated by the search for the database of TIGR (The Institute for Genomic Research). It was found that gene locus HP1037 of *Helicobacter pylori* 22695 coded the homologous protein.

From the results, the cloning of the protein of this invention was performed. Namely, *Helicobacter pylori*

60190 was used as a template, firstly, conveniently plural groups of suitable primers based on gene locus HP1037 and gene locus HP1036 of the upstream and gene locus HP1038 of the downstream were formed (at 5' site and 3' site) to perform sequening. DNA polymerase having proofreading function was used. Each group of primers was constituted so as to contain sufficient mutual primer parts, and plural sequencings from 5' site and 3' site were performed. The resulting DNA sequences were shown in SEQ ID No. 2 of the sequence listing. The amino acid sequences were shown in SEQ ID No.1.

Example 3

Expression Experiment of the Toxic Protein by Gene Recombination

E. coli was used in the expression experiment. Vector pET-30EK/LIC (producted by Novagen Co.) and E. coli BL21 (DE3) for expression were used. The sense primer was SEQ ID No.3 inserting GACGACGACAAG at 5' site of the sense chain to the code of the toxic protein derived from Helicobacter pylori 60190 that was cloned in Example 2. The antisense primer was SEQ ID No.4 inserting GAG-GAGAAGCCCGGTTA at 5' site. Inserting genes were formed by a PCR method by using the above primers. The inserted genes were prepared in the presence of 25 mM dATP and 100 mM DTT with T4 DNA polymerase to fit for LIC site of the vector and warmed in the presence of 25 mM EDTA. The formed recombinant was again sequenced to confirm that was identical with SEQ ID No. 1. It was further transformed into E. coli BL21 (DE3) for expression, and cultured in a LB medium conting 30 µg/ml of kanamycin.

Figure 2:
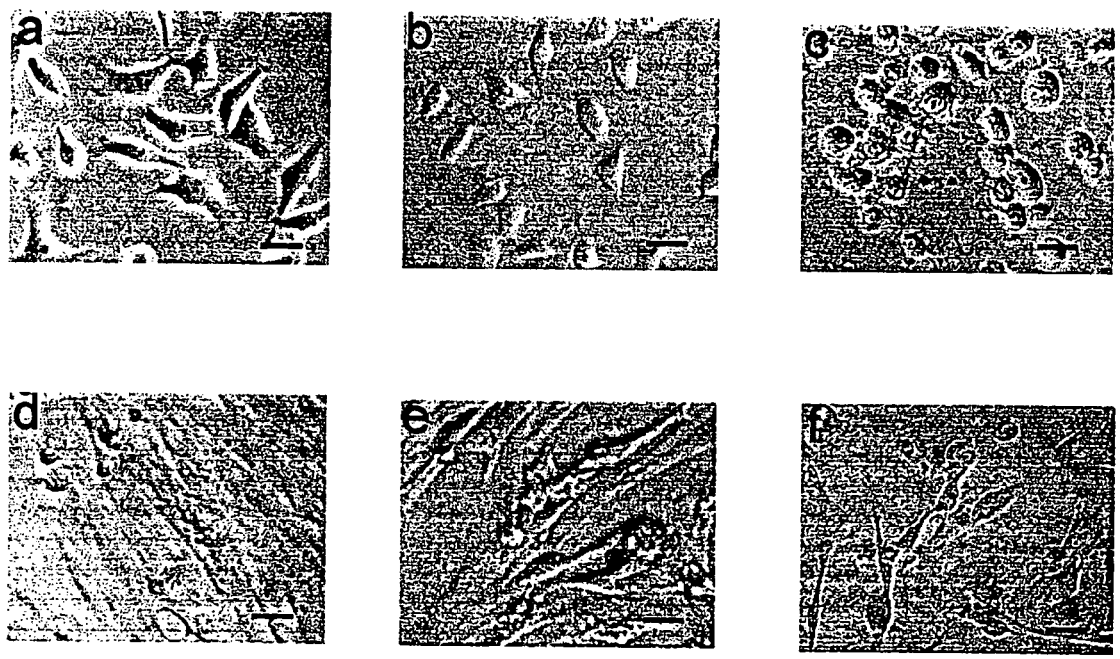
FIG. 2 shows cell morphologic change with the gene recombinant toxin obtained in Example 3. a shows a negative contlol of HeLa cells after 6 hours. b and c show HeLa cells after 3 hours and after 6 hours of 5 nM addition of recombinant M toxin. d shows CRL7407(ATCC) normal human gastric cells of negative control after 6 hours. e and f show CRL7407 cells after 3 hours and 6 hours of 5 nM addition of recombinant M toxin.
Figure 3:
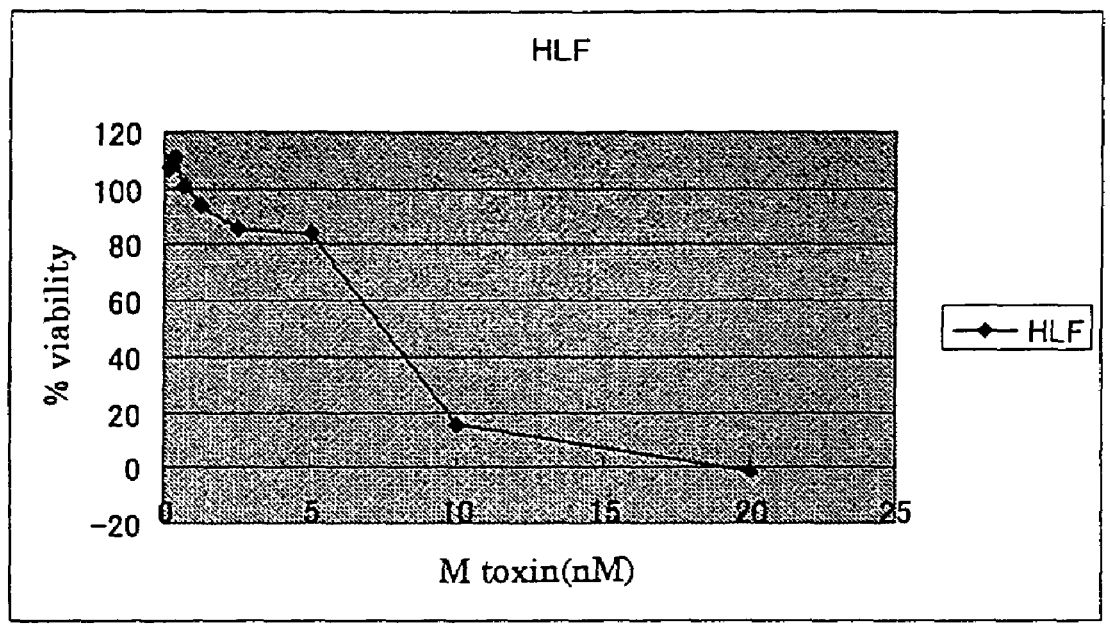
FIG. 3 shows sensitivity for M toxin of several kinds of cancer cells in Example 3. It was determined by a WST method. X axis shows concentration of M toxin in a substrate, and Y axis shows directly absorbance of wavelength 415 nm or by a relative ratio when the absorbance of a negative control is estimated as 100%. HLF: rat hepatoma. colon 26: carcinoma of the mouse colon.
Figure 3:
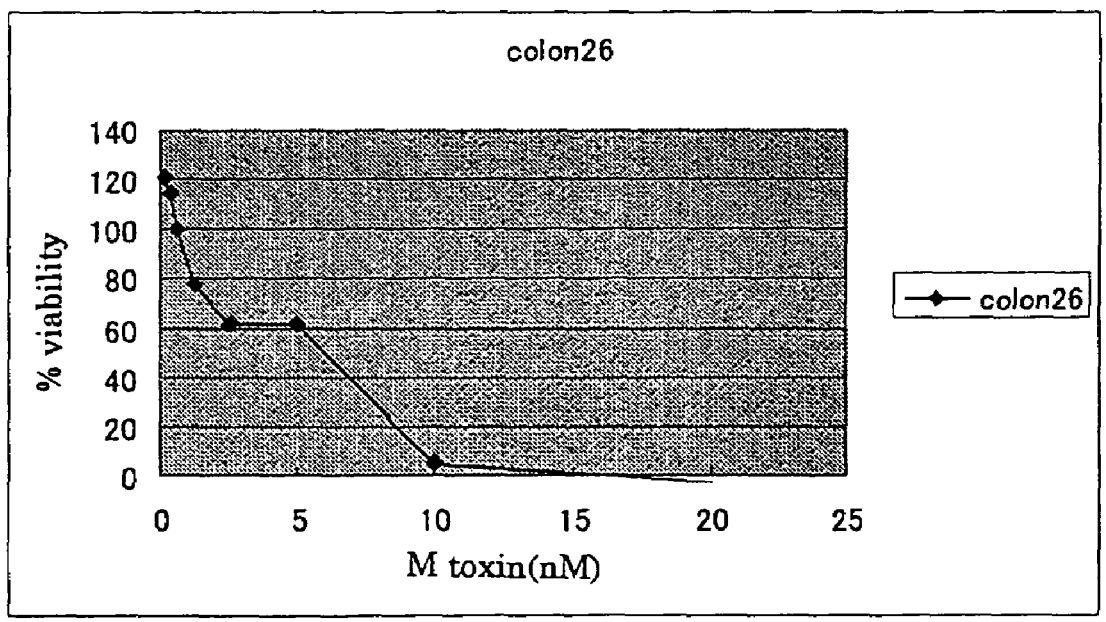
Figure 4:
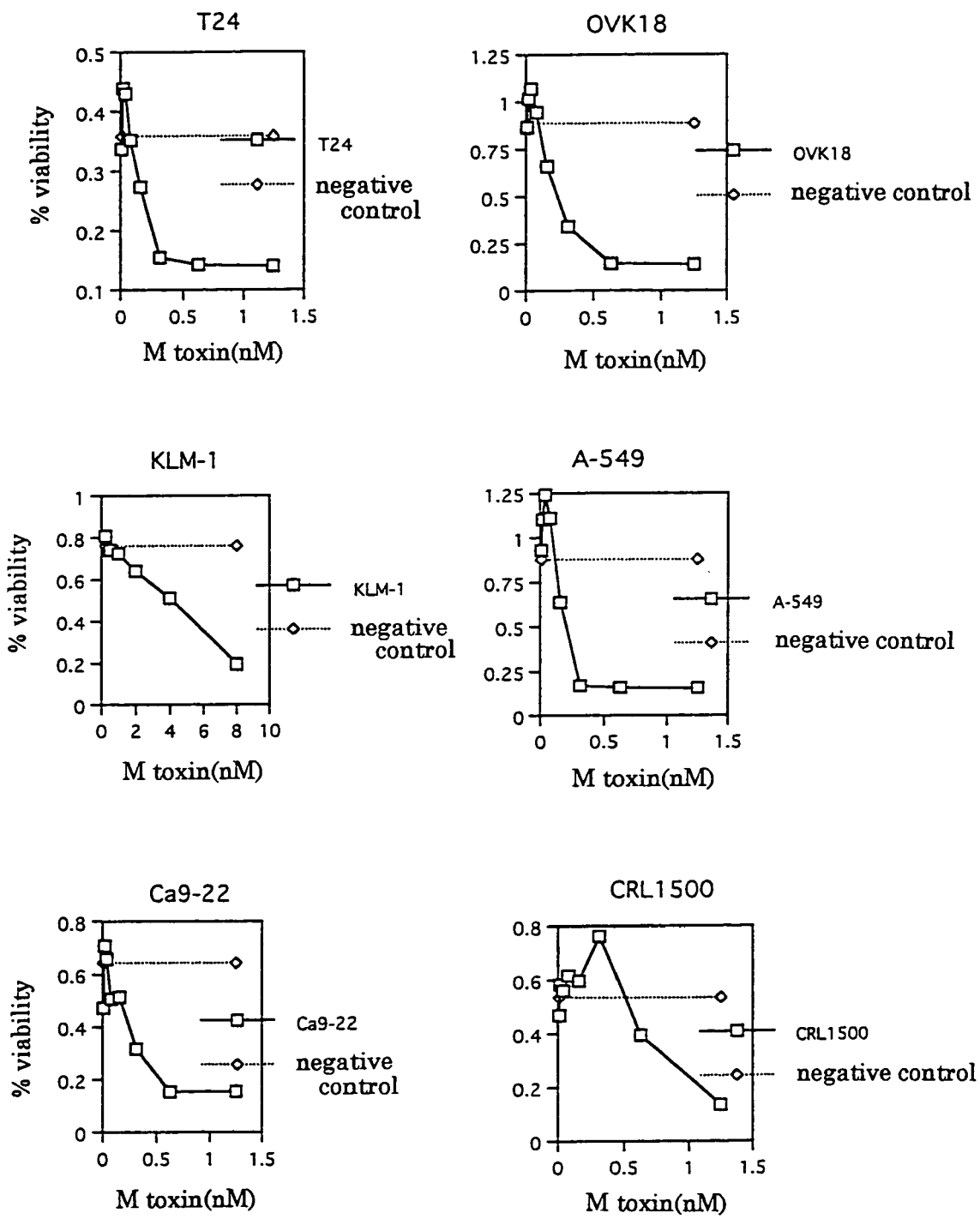
FIG. 4 is as shown in FIG. 3. T24: human cancer of the bladder. OVK18: human ovarian cancer. KLM-1: human pancreatic cancer. A-549: human lung cancer. Ca9-22: human cancer of the gum. CRL1500: human cancer of the breast.
Figure 5:
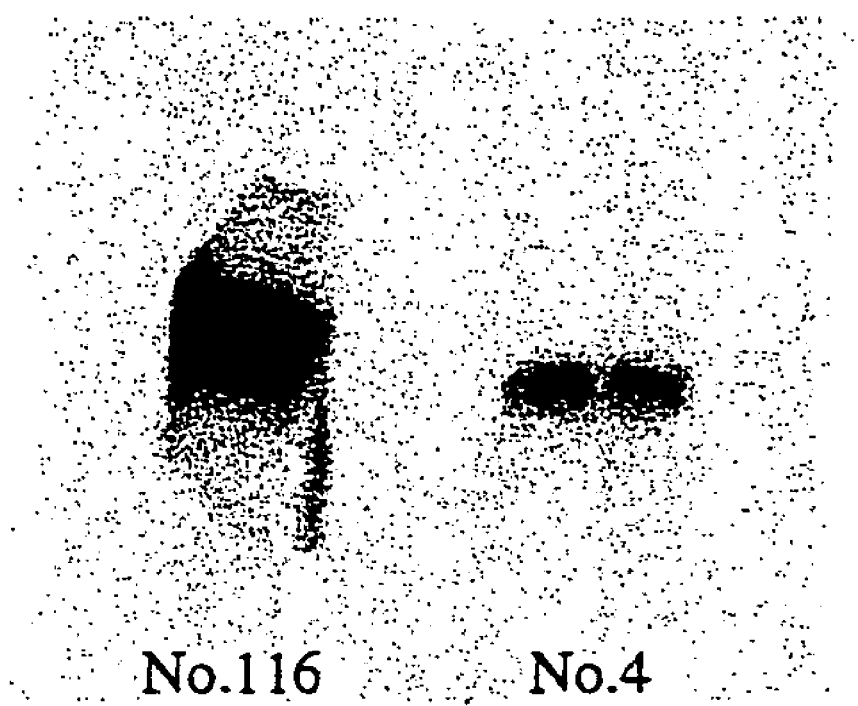
FIG. 5 shows western blotting of monoclonal antibody which is conducted in Example 8. All dilution magnifications of cultured supernatants of hybridoma cells are 20 times.
Figure 5:
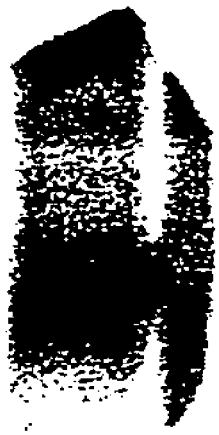
Figure 6:
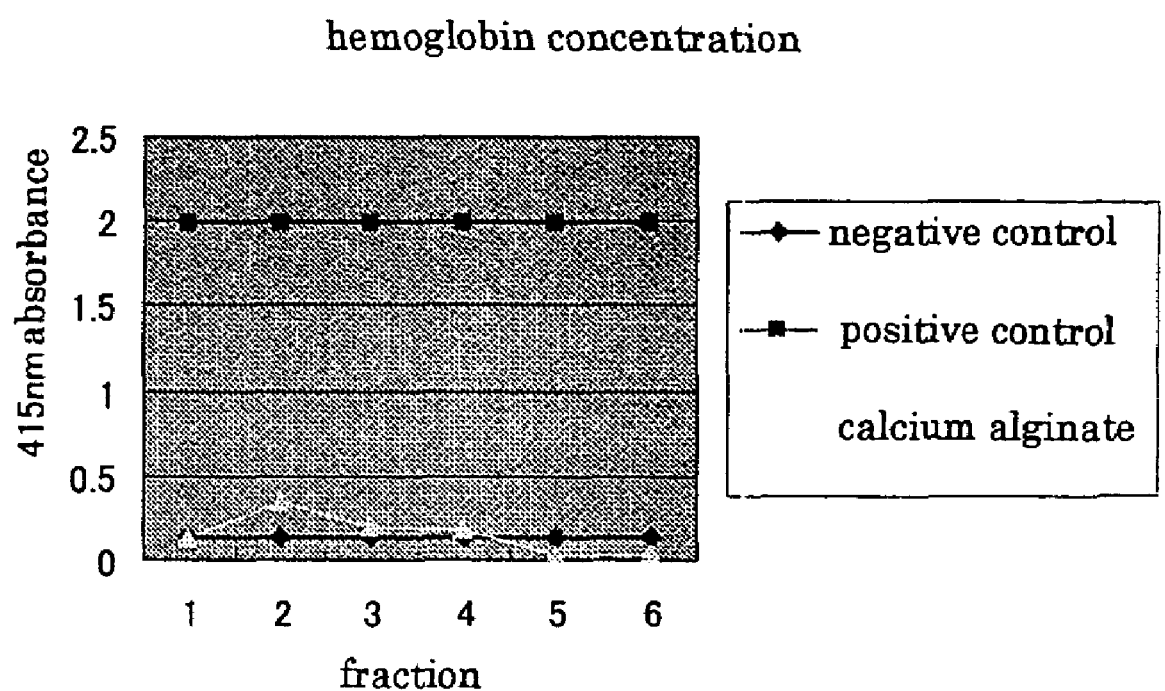
FIG. 6 shows M toxin activity with calcium alginate as an adsorbent in Example 9. The negative control contains 10 mM Tris buffer pH7.7 alone as a substrate, and the positive control contains a substrate and 10 mM M toxin. X axis shows each fraction numaber passed through a calcium alginate column. An average concentration of each fraction is 10 nM. and any one of the fractions shows at least 10 nM or more. When red corpuscles are destroyed, hemoglobin concentration in the solution is increased. Y axis shows 415 nm absorbance.
Figure 7:
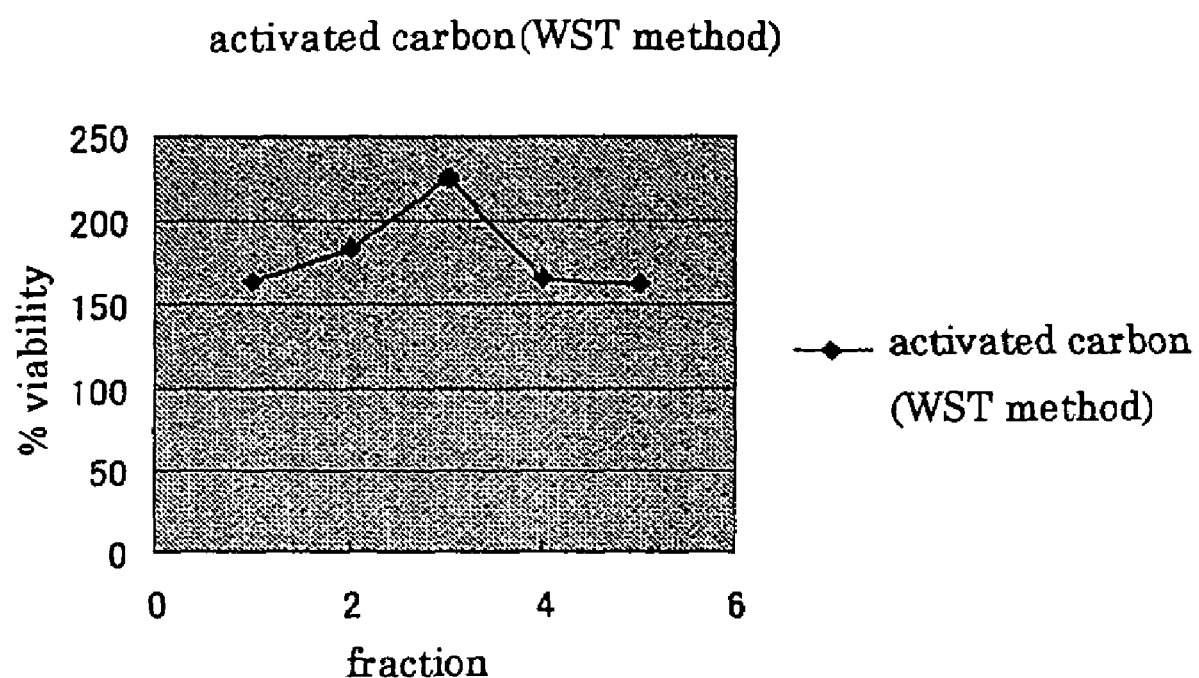
FIG. 7 shows, in Example 10, % viability of HeLa cells showing M toxin inhibition activity by adsorption of activated carbon in Example 10. X axis shows each elute fraction number of column. M toxin concentrations are average 10 nM and any one of them is at least 10 nM or more. Y axis shows % obtained by dividing the value of the toxicity of each fraction by a positive control which is measured by a WST method.
Figure 8:
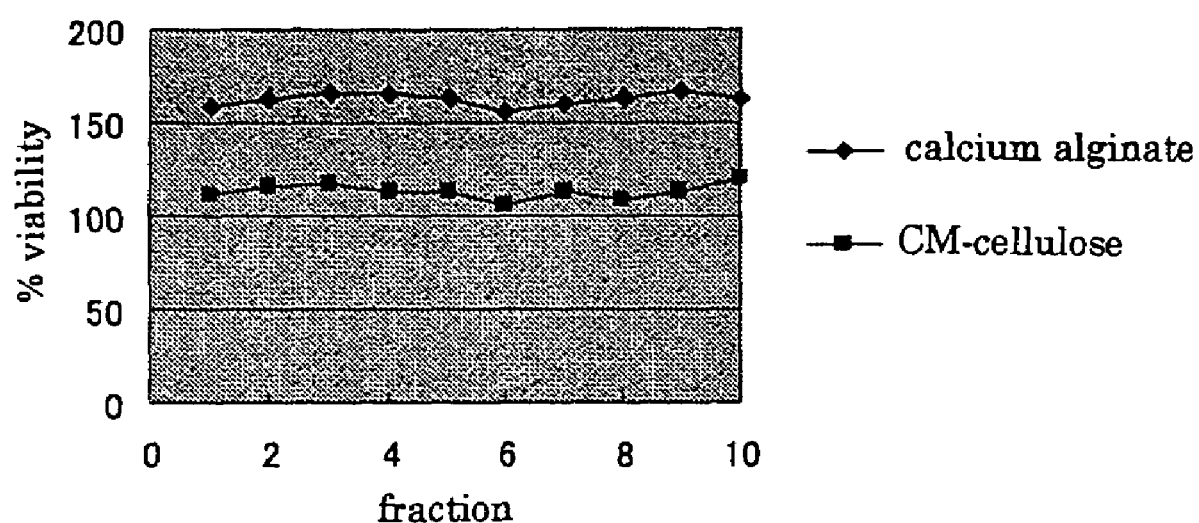
FIG. 8 shows as shown in FIG. 7. It shows % viability in HeLa cells of CM-cellulose and calcium alginate showing M toxin inhibition activity by adsorption in Example 10.

Shake culture was conducted to obtain about 0.4 of $OD_{600}$ at a temperature of 37° C. at 250 rpm. Isopropyl-beta-thiogalactoside was added to obtain the final concentration of 1 mM, and further the mixture was shaked for 2 hours. Since the fused protein formed an inclusion body, E. coli was collected with centrifugation, and the inclusion body of the protein was obtained with a BugBuster reagent and Benzonase Nuclease (both are available from Novagen Co.). The protein was separated by an electrophoresis method of sodium dodecyl sulfate-polyacrylamide gel (SDS-PAGE), and the corresponding single band was confirmed by silver stain. The protein was then refolded and compared with the control with a WST reagent (Dojin Chemical Laboratories Ltd. Cell Counting Kit) by using HeLa cells and the other warm-blooded animal cells. As the results, significant differences of survival were evaluated, and it was found that the expression protein had equal activities to those of purified protein. It was found that the expression protein had the same activities to the normal human gastric cells as HeLa cells of cervical cancer cells. (FIG. 2). It was also found that not only to the other human tissues, but also to manmalian cells the protein had broad activities. (FIG. 3, FIG. 4).

Example 4

Forming of Monoclonal Anti-M Toxic Antibody:

Expression M toxin 240 µg, which had been refolded, was subcutaneously administered two times at several positions of BALB/C mouse. After 4 days of final immunization, the mouse spleen was excised and press filtered with stainless meshes, and suspended on Eagle's modified minimum essential medium (MEM) to obtain a suspended solution of spleen cells. As the cells used for cell fusion, Myeloma cells P3-X63. Ag 8. U1 (P3U1) derived from BALB/C mouse was used as the cells used in the cell fusion. [Current topics in microbiology and immunology, 81, 1(1978)$_o$. The cell fusion was conducted in accordance with the origin method [Nature, 256, 495 (1975) ]. Namely, spleen cells and P3U1 were washed respectively with MEM not containing serum three times and mixed at 6.6:1 of a ratio of spleen cells and P3U1 numbers. Cells were precipitated by centifugation at 750×g for 15 minutes. All of the supernatant was removed, and the precipitate was unfastened, 0.3 ml of 45% polyethylene glycol (PEG) 6000 (Producted by Wako Junyaku Co.) was added, and the mixture was permitted to stand in a warm water tank of 37° C. for 7 minutes to perform the fusion. After the fusion, MEM in limited amounts was added to the cells, and MEM of total 15 ml was added. The mixture was centrifuged at 750×g for 15 minutes and the supernatant was removed. The cell precipitate was suspended in GIT medium (produced by Wako Junyaku Co.) (GIT-10% FCS) containing 10% bovine fetal serum to obtain P3U1 of $2\times10^5$ per 1 ml, and seeded into 24-well multi dishes (producted by Iwaki Co.) at 1 ml per well in 168 wells. After seeding, the cells were incubated in 5% carbon dioxide incubator at a temperature of 37° C. After 24 hours, GIT-10% FCS medium (HAT medium) containing HAT (hypoxanthin $1\times10^{-4}$M, aminopterin $4\times10^{-7}$M and thymidine $1.6\times10^{-3}$M) was added at 1 ml per well to initiate HAT selective cultivation. After 4 and 7 days, 1 ml of the old liquid was discurded and the HAT selective cultivation was continued by adding 1 ml of the HAT medium. Multiplication of hybridoma was found after 9 days of the cell fusion, and the supernatant was collected. The antibody value on the supernatant was determined by the following method. Namely, the culture supernatant 100 µl and HRP-labelled M toxin 100 µl, which is diluted to 200-fold with buffer C, were added into each well of microplates binding anti-mouse immunoglobulin antibody, and reacted overnight at a temperature of 4° C. After the plates were washed with PBS, to make microplates binding anti-mouse immunoglobulin antibody, firstly, a 0.1M carbonate buffer solution, pH9.6 containing goat anti-mouse immunoglobulin antibody (IgG fraction, producted by DAKO Co.) 100 µg/ml was pipetted into 96-well microplates at 100 µl per plate, and is permitted to stand for 24 hours at a temperature of 4° C. Then, the plates were washed with phosphate-buffered saline (PBS, pH7.4), 25% Brock Ace (trademark, producted by Yukijirushi Mlk Products Co.) and PBS, pH7.2 containing 0.1% $NaN_3$ were pipetted at each 3001 to block excess binding parts of the well and treated for at least 24 hours at a temperature of 4° C. To each well of the above microplates binding anti-mouse immunoglobulin antibody, mouse antiserum 100 µl, which is diluted with buffer EC [0.02M phospahte buffer, pH7.0 containing 0.2% BSA, 0.4 M NaCl, 0.4% Brock Ace, 0.05% CHAPS (3-[(3-cholamidopropyl) dimethyl-ammonio]-1-propanesulfonate), 2 mM EDTA and 0.1% $NaN_3$], was added and reacted for 16 hours at a temperature of 4° C. Then, the plates were washed with PBS, pH7.4, and HRP-labelled refolding toxin protein 100 µl was added and reacted for 7 hours at room temperature. The above refolding toxin protein was prepared in the above Example 3 by diluting to 100-fold with buffer C [0.02M phosphate buffer, pH7.0, containing 1% BSA, 0.4 M NaCl and 2 mM EDTA]. The plates were then washed with PBS, pH7.4, a TMB microwell peroxidase substitute system (KIRKEGAARD & PERRY LAB. available from Funakoshi Yakuhin) 1001 µl was added, and reacted at room temperature for 10 minutes to determine the enzyme activity on the solid phase. After the reaction was stopped by adding 1M phosphoric add 100 µl, the absorbance at 450 nm was determined with a plate reader (MTP-120, producted by Corona Co.). According these methods, the enzyme activity on the solid phase was determined. As the results, 18 wells that the antibody value is found were selected from 123 wells, and the hybridomas were frozen and stored. Hybridomas of 6 wells, No. 4, No. 53, No. 61, No. 76, No. 101 and No. 116 were cloned by dilution method. In the cloning, thymocytes of BALB/C mouse as feeder cells were added at $5 \times 10^5$ per well After the cloning, the antibody value of the supernatant was determined by the same method. Positive clones were No. 4, No. 101 and No. 116. These clones were as antibody-producing hybridomas of expression M toxin.

Example 5

Determination of a Class and a Subclass of Monoclonal Antibodies:

By the method described in Example 4, anti-rabbit IgG-binding micro plates were formed. Namely, 0.1M carbonate buffer containing goat anti-pH9.6 was pipetted into 96-well microplates at 100 μl per well and left at a temperature of 4° C. for 24 hours. The plates were then washed with phosphate-buffered saline (PBS, pH7.4), 25% Block Ace (trademark, producted by Yukijirushi Milk Products Co.) and PBS, pH7.2 containing 0.1% NaN$_3$ were pipetted at each 300 μl to block excess binding parts of the well and treated for at least 24 hours at a temperature of 4° C. To the anti-rabbit IgG antibody-binding microplates, buffer EC 50 μl and subtype specific antibody 100 μl containing in an iso-type typing kit producted by Bio-Rad Laboratories were added to react for one day at a temperature of 4° C. After the plates were washed with PBS, pH7.4, the culture supernatant of the hybridomas described above was added and reacted for one day at a temperature of 4° C. The plates was washed with PBS, pH7.4, and HRP-labelled refolding toxin protein 100 μl, which was prepared in the above Example 3 by diluting to 100-fold with buffer C [0.02M phosphate buffer, pH7.0, containing 1% BSA, 0.4 M NaCl and 2 mM EDTA], was added and reacted for 6 hours at room temperature. The plates were washed with PBS, pH7.4, and the enzyme activity on the solid phase was determined by the method described in Example 4. As the results, the subclasses of the monoclonal antibody porduced by these hybridomas were No. 4 (IgG1), No. 101 (IgG2 b) and No. 116 (IgG2a).

Example 6

A Method for Producing Mouse Ascites Fluid of Hybridoms:

Hybridomas, No. 4, No. 101 and No. 116 were mouse ascites. Mineral oil 0.5 ml was parentherally administered to mice, previously. To the mice (BALB/C, female), the above s were parentherally sdministered at 1-3×10$^6$ cells/mouse, and the ascites containing the antibody were collected after 6-20 days. The monoclonal antibody was purified from the obtained ascites with a protein-A column. Namely, the ascites about 25 ml were diluted with the same volume of binding buffer (3.5M NaCl, 1.5M glycin containing 0.05% NaN$_3$, pH9.0), the solution was precipitate to a recombinant protein-A-agalose (Repligen Co.) column that was previously equilibrated with binding buffer, the specific antibody was eluted with elution buffer (0.1M citric acid buffer, pH3.0 containing 0.05% NaN). The elution liquid was dialyzed with PBS, pH7.4 at a temperature of 4° C. for 2 days, and filtered for removing bacilli with a filter of 0.22 μm (producted by Millipore Co.) or stored at a temperature of −80° C.

Example 7

Preparation of Polyclonal Antibody M Toxin

Cytotoxic protein M toxin of this invention 4.1 mg was mixed with Freund's complete adjuvant and the mixture was subcutaneously immunized to a rabbit. After one week, the same amount of the M toxin was mixed with Freund's incomplete adjuvant and the mixture was further subcutaneously immunized to the rabbit. After the immunization, collected blood was centrifuged to remove hemocyte components, and anti-serum was obtained.

Example 8

Analysis of M toxin by Western Blotting:

SDS-Sample Buffer containing 2-mercaptoethanol was added to the supernatant obtained in Example 3, the mixture was electrophoresed with Peptide-PAGE (TEFCO) and electrically transferred to a PVDFmemmbrane (Amersham). Each antibody (2 µg/ml) obtained in Example 4 and Example 6 was used as primary antibody. HRP (Horseradish peroxidase)-labelled-anti-rabbit and anti-mouse IgG antibodies (2000-fold dilution; Dako) was used as secondary antibody. The coloration was performed with an ECL Western Blot Detection System (Amersham). As the results, it was confirmed that each primary antibody recognized the expression protein. (FIG. 5).

Example 9

Active carbon (0.2~0.1 mm of diameter), CM cellulose and calcium alginate, each 0.5 ml, were charged in three colums. After equilibrating with Tris buffer 10 mM, pH7.7, 0.5 ml of M toxin 400 nM having refolded activity was added into each column, and these column was plugged and allowed to stand for 60 minutes at a temperature of 25° C. Meanwhile, Tris buffer alone and Tris buffer containing the same M toxin were allowed to stand under the same conditions. All columns were then opened, each 100,u 1 dropping from columns was separated, further, each Tris-buffer 0.5 ml was added to each column, and each 100 µl was collected. Whole blood of normal adults was centrifuged 2-3 times at 800×g for 10 minutes until the supernatant became transparent. The precipitated erythrocytes 10 µl added to 10 mM Tris buffer 990 µl was used as a positive control. Similarly, the precipitated erythrocytes 10 µl added to 0.9% salt 10 mM Tris buffer was used as a negative control. Samples were collected from the above columns. Erythrocytes of 1 volume per 100 volume of the sample were added to the samples. The controls and the samples were compared by the eluted hemoglobin relative concentration with a multiple plate reader (Biorad) by measuring as an absorbance of 415 nm. (FIG. 6).

Example 10

The ratios that HeLa cells (human cancer cells of the uterine cervix) were exposed to the fractions from each columns of Example 9 and the viability were determined by a WST method using a tetrazolium salt. HeLa cells were cultured in 96-well plates for 24 hours at a ratio of 10000 cells per well. A negative control of culture liquid only, each sample liquid, and a positive control of 20 nM of the toxin protein were respectively added to each well, and thsese were cultured for 12 hoursat at a temperature of 37° C. Using a Cell Counting Kit (DOJIN LABORATORIES Ltd. Co.), the ratios of cell viability detected by a WST method were measured as an absorbance of 415 nm wavelength. (FIG. 7, FIG. 8).

INDUSTRIAL APPLICABILITY

The protein and the partial peptide of this invention and the like can be used, for example, as treating agents of cancers. The antibody of this invention can be used to identify the protein of this invention in the blood, tissues, urine and excrements collected from test patients and to confirm the *Helicobacter pylori* infection. It is further used for quantification of the protein of this invention. The protein of this invention can be used as a screening agent of the compounds increasing or inhibiting the activities of the protein of this invention.

The invention claimed is:

1. An isolated cytotoxic protein comprising a protein having the amino acid sequence represented by SEQ ID NO:1.

2. The isolated cytotoxic protein of claim 1, wherein the protein is produced with *Helicobacter pyloici*.

3. The isolated cytotoxic protein of claim 1, wherein the protein is obtained by culturing a transformant which is transformed with a recombination vector containing DNA of SEQ ID NO:2 coding said cytotoxic protein.

4. The isolated cytotoxic protein of claim 3, wherein the transformant is deposited by deposition No. FERM BP-8218 at the International Patent Organism Depository, National Institute of Advanced Industrial Science and Technology.

5. A composition comprising said isolated cytotoxic protein of claim 1 and a pharmaceutically acceptable carrier.

6. A kit for screening a compound or a salt thereof that inhibits the activity of the isolated cytotoxic protein of claim 1, comprising said isolated cytotoxic protein.

* * * * *